United States Patent
Wang et al.

(10) Patent No.: US 12,360,021 B2
(45) Date of Patent: Jul. 15, 2025

(54) GRAPHENE OXIDE AFFINITY SAMPLE GRIDS FOR CYRO-EM

(71) Applicant: The Regents of the University of California, Oakland, CA (US)

(72) Inventors: Feng Wang, Fremont, CA (US); David Agard, Burlingame, CA (US); Yifan Cheng, San Francisco, CA (US); Eugene Palovcak, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1097 days.

(21) Appl. No.: 17/269,466

(22) PCT Filed: Aug. 19, 2019

(86) PCT No.: PCT/US2019/047075
§ 371 (c)(1),
(2) Date: Feb. 18, 2021

(87) PCT Pub. No.: WO2020/041202
PCT Pub. Date: Feb. 27, 2020

(65) Prior Publication Data
US 2021/0310910 A1    Oct. 7, 2021

Related U.S. Application Data

(60) Provisional application No. 62/720,043, filed on Aug. 20, 2018.

(51) Int. Cl.
*G01N 1/28* (2006.01)
*C01B 32/198* (2017.01)
(Continued)

(52) U.S. Cl.
CPC ......... *G01N 1/2813* (2013.01); *C01B 32/198* (2017.08); *G01N 1/42* (2013.01);
(Continued)

(58) Field of Classification Search
None
See application file for complete search history.

(56) References Cited

U.S. PATENT DOCUMENTS

| 2008/0220456 A1 | 9/2008 | Williams et al. |
| 2011/0226960 A1* | 9/2011 | Zhang ............. H01J 37/20 250/440.11 |

(Continued)

FOREIGN PATENT DOCUMENTS

| WO | 2016193746 A1 | 12/2016 |
| WO | WO-2017106797 A1 * | 6/2017 ......... C01B 32/192 |
| WO | 2018106761 A1 | 6/2018 |

OTHER PUBLICATIONS

Benjamin et al. (2016) "Selective Capture of Histidine-tagged Proteins from Cell Lysates Using TEM grids Modified with NTA-Graphene Oxide" Scientific Reports, 6:32500, 11 pages.

*Primary Examiner* — Colin W. Slifka
(74) *Attorney, Agent, or Firm* — Brian E. Davy; Mandar A. Joshi; Bozicevic, Field & Francis LLP

(57) ABSTRACT

Herein are innovations that enable facile cryo-EM analysis of diverse samples. Methods of functionalizing sample grids for cryo-EM are described, including methods of creating high quality graphene oxide films on cryo-EM substrates. The cryo-EM sample substrates are functionalized with affinity molecules that efficiently concentrate sample molecules and other specimen types on the grid, away from the air-water interface. Affinity groups include amines and proteins such as tagging system proteins and peptides that can be used to capture diverse sample types with high affinity.

(Continued)

Optionally, spacers such as PEG chains are used to place sample particles away from the substrate surface, reducing substrate-induced artifacts.

11 Claims, 10 Drawing Sheets

Specification includes a Sequence Listing.

(51) Int. Cl.
  *G01N 1/42* (2006.01)
  *G01N 23/2202* (2018.01)
  *G01N 23/2204* (2018.01)
  *G01N 23/2251* (2018.01)
  *G01N 33/543* (2006.01)
  *H01J 37/20* (2006.01)

(52) U.S. Cl.
  CPC ..... *G01N 23/2202* (2013.01); *G01N 23/2204* (2013.01); *G01N 23/2251* (2013.01); *G01N 33/54366* (2013.01); *H01J 37/20* (2013.01)

(56) References Cited

U.S. PATENT DOCUMENTS

| | | |
|---|---|---|
| 2013/0277573 A1 | 10/2013 | Miller et al. |
| 2018/0017558 A1 | 1/2018 | Terfort et al. |
| 2019/0003999 A1* | 1/2019 | Thompson ............. H01J 37/20 |

* cited by examiner

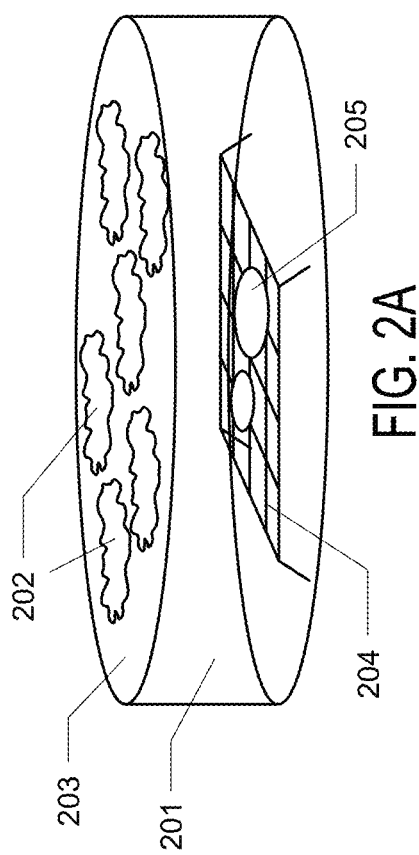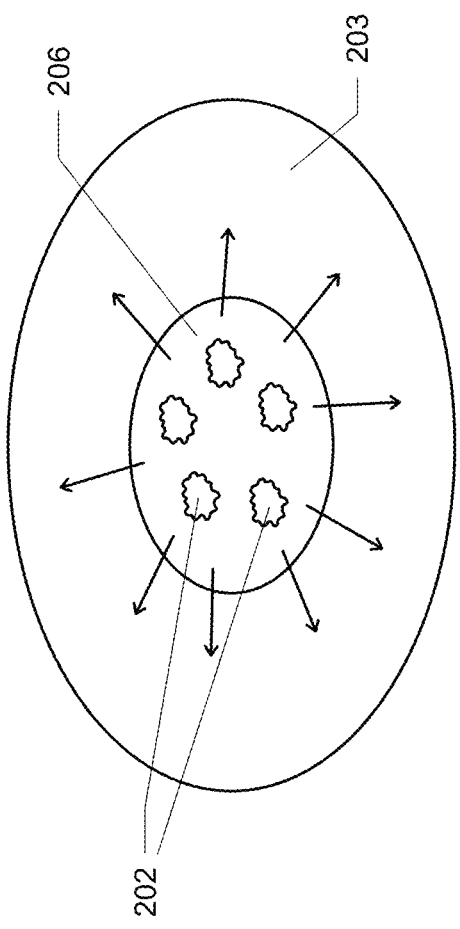

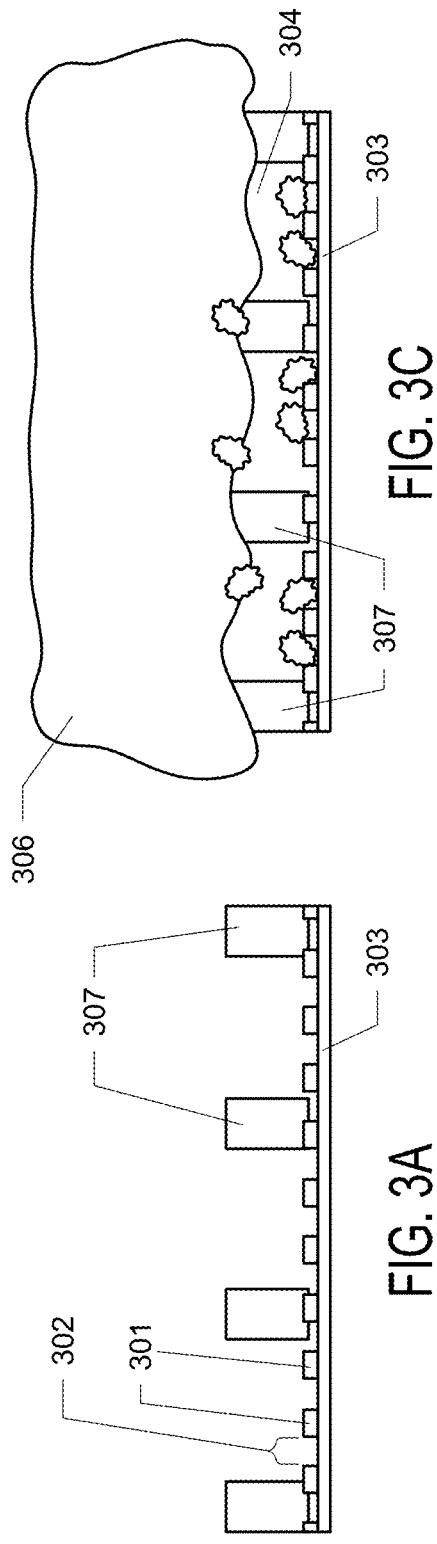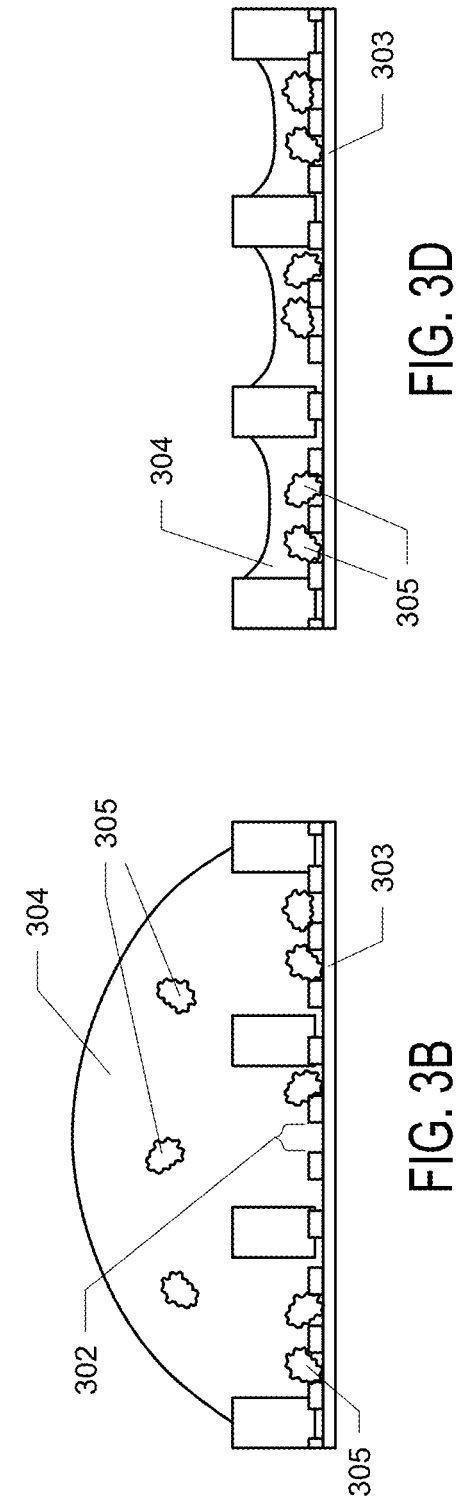

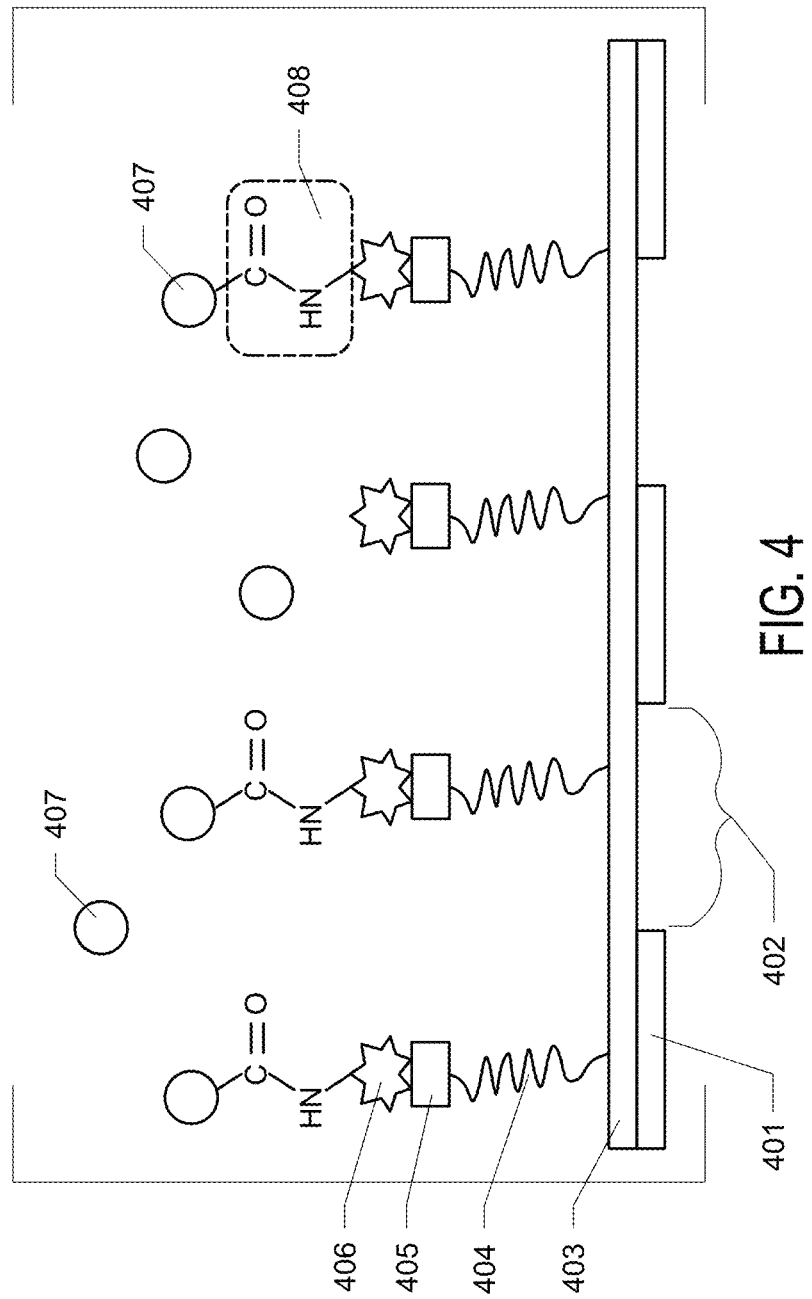

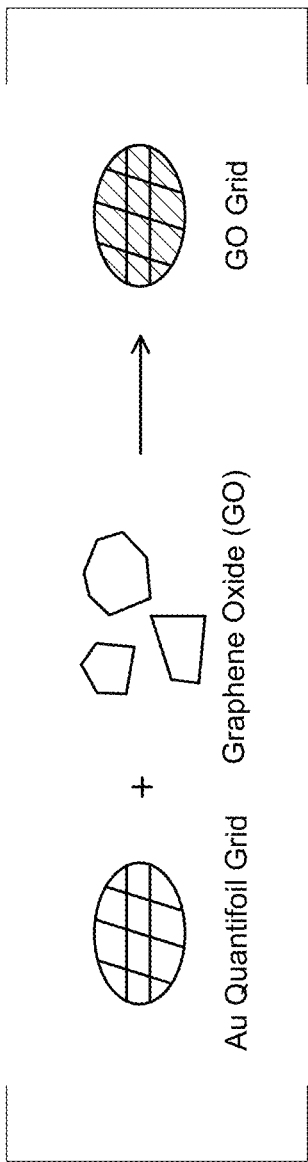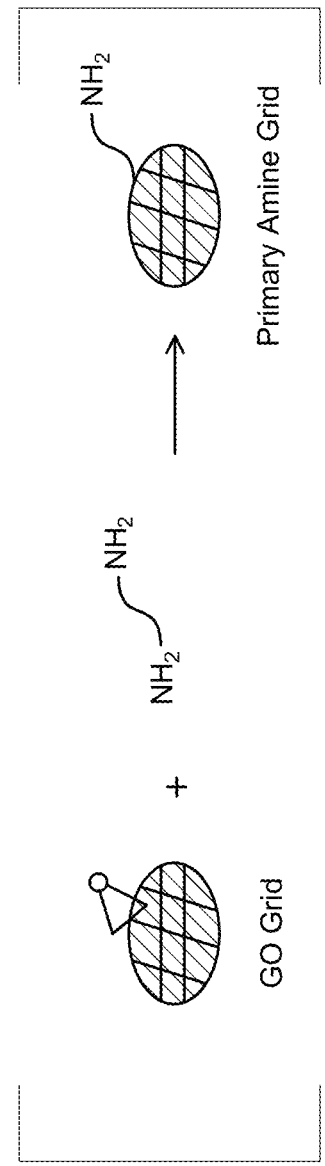
FIG. 5A
FIG. 5B

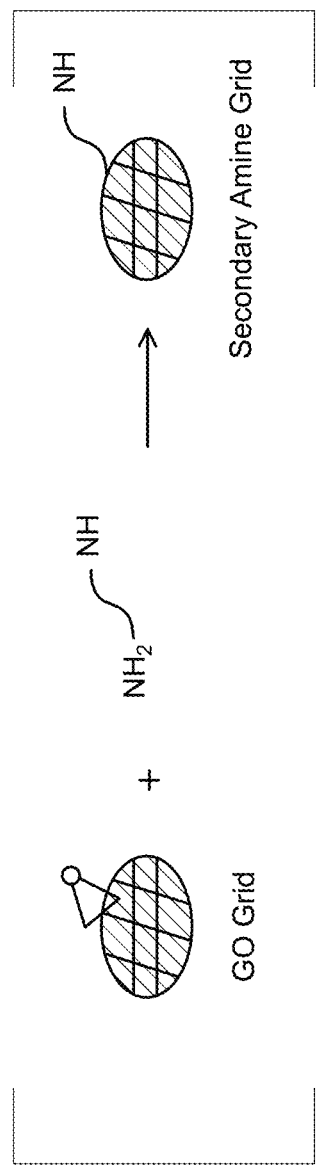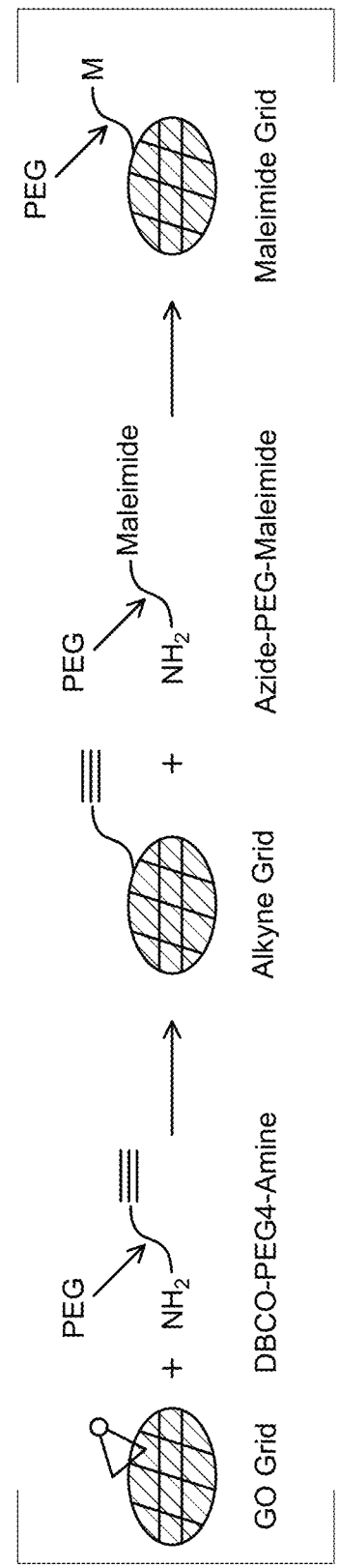

GRAPHENE OXIDE AFFINITY SAMPLE GRIDS FOR CYRO-EM

CROSS-REFERENCE TO RELATED APPLICATIONS

This application is a § 371 National Stage Application of International Patent Application Number PCT/US2019/047075, entitled "Graphene Oxide Affinity Sample Grids for Cryo-EM," filed Aug. 19, 2019, which claims the benefit of priority to U.S. Provisional Application Ser. No. 62/720,043 entitled "High Quality Graphene Oxide Cryo-EM Sample Grids," filed Aug. 20, 2018, the contents of which applications are hereby incorporated by reference.

STATEMENT REGARDING FEDERALLY SPONSORED RESEARCH OR DEVELOPMENT

This invention was made with government support under grant number U54 CA209891 awarded by the National Institutes of Health. The government has certain rights in the invention.

REFERENCE TO SEQUENCE LISTING, A TABLE, OR A COMPUTER PROGRAM LISTING COMPACT DISK APPENDIX

The instant application contains a Sequence Listing which has been filed electronically in ASCII format and is hereby incorporated by reference in its entirety. Said ASCII copy, created on Aug. 19, 2019, is named UCSF068PCT_SL.txt and is 6,143 bytes in size.

BACKGROUND OF THE INVENTION

Transmission electron microscopy (TEM) is a versatile technique that can provide high resolution structural information for biological specimens. Cryogenic electron microscopy (cryo-EM) is a powerful and precise method for structural analysis of macromolecules. Cryo-EM has the potential to resolve protein structures at a near-atomic or atomic resolutions.

Cryo-EM specimens are typically prepared by depositing purified proteins onto cryo-EM grids, which usually consist of a metal grid covered with continuous perforated carbon or gold films. After removing excessive sample solutions through blotting, the grid is plunged into liquid ethane and the biological samples are vitrified in amorphous ice. Proteins of interest are thus preserved in essentially their native hydrated, aqueous state.

With quality samples, cryo-EM enables rapid data collection and processing, and the resolution of protein structures, or of other macromolecules, at very high resolutions. However, cryo-EM sample preparation remains a slow and inefficient process, and in many cases is rate-limiting in the application of cryo-EM. For challenging systems and dynamic complexes, the typical process of sample preparation is problematic, either because the system cannot be reconstituted, or aggregation of the sample particles may occur. Perhaps even more significant is the disruption of protein structure and protein-protein interactions that can occur when samples in the cryo-EM grid become exposed to the air-water interface. During the formation of the very thin vitreous ice films (often <50 nm) required for high resolution imaging, the high surface area to volume ratio of the buffer just prior to freezing dramatically increases the probability of samples being exposed to or being in proximity to the denaturing interface. Indeed, most particles in cryo-EM sample grids are observed at the air-water interface and are not usable due to the distortions caused thereby. The air-liquid interface leads to preferential, non-random orientation of the macromolecules at the interface, and furthermore, damage or denaturation of the macromolecules at the air-liquid interface renders them unusable for imaging. Thus, in conventional sample systems, high resolution structures can only be obtained from a small subset of the particles. Accordingly, the full potential of cryo-EM cannot be realized until the poor efficiency of conventional sample preparation methods is overcome.

A potential solution to both the sample preparation and air-water interface problems is through the use of "affinity grids" that would simultaneously concentrate the sample on the grid while restricting it from the air-water interface. Several affinity grid strategies have been put forward for cryo-EM. One proposed solution is the decoration of a supporting film with nickel-nitrilotriacetic acid (Ni-NTA) to capture His-tagged proteins, for example, as described in: Llaguno et al. Chemically functionalized carbon films for single molecule imaging, *Journal of structural biology* 185, 405-417 (2014); Kelly et al., Monolayer purification: A rapid method for isolating protein complexes for single-particle electron microscopy, *Natl. Acad. Sci. USA* 105, 4703-4708 (2008); and Liu et al. Bioactive Functionalized Monolayer Graphene for High-Resolution Cryo-Electron Microscopy, *J. Am. Chem. Soc.* 141, 4016-4025 (2019). Another attempted solution is the use of 2D streptavidin crystals to capture biotin or strep-tagged proteins, for example, as described in Han et al., Electron microscopy of biotinylated protein complexes bound to streptavidin monolayer crystals, *Journal of structural biology* 180, 249-253 (2012). Another approach that has been tested is the use of a supporting grid functionalized with specific antibodies to capture and concentrate targets of interest. For example, antibody capture of viruses has been demonstrated, as described in Kelly et al., Strategy for the Use of Affinity Grids to Prepare Non-His-Tagged Macromolecular Complexes for Single-Particle Electron Microscopy, *Mol. Biol.* 400, 675-681 (2010) and Yu, G. M. et al. Single-step antibody-based affinity cryo-electron microscopy for imaging and structural analysis of macromolecular assemblies, *Journal of structural biology* 187, 1-9 (2014).

Overall, the previously attempted affinity grid approaches have not proven to be broadly useful. For example, His-tags are not sufficiently efficient to capture targets of interest in sufficient quantity without massive concentrations of the sample protein or other target moiety, which in itself leads to particle aggregation and artifacts. The prior art support films are thick and the resultant electron scattering unacceptably reduces the quality of target resolution. Antibodies are promising in theory, however, the use of specific antibodies for each target sample molecule means that the approach must be laboriously implemented for each specific target, which is especially problematic for targets lacking quality antibodies.

Another challenge in the development of cryo-EM affinity grid systems is preventing artifacts produced by the sample substrate. Immobilization of target species on the sample substrate provides a means of concentrating samples away from the air-water interface at the top of the ice layer. However, interactions with the sample substrate can introduce additional, undesirable artifacts. Interactions between the sample proteins, or other species of interest, and the substrate can affect the conformation, stability, and orientation of the sample particles and can negatively affect the EM resolution of the target molecules. Accordingly, novel sample preparation approaches are required that avoid artifacts from both the air-water interface at the top of the ice layer, and substrate-sample interactions at the bottom of the ice.

Accordingly, there remains a need in the art for novel sample preparation systems for cryo-EM specimens. There remains a need in the art for systems that can position samples at a distance from the air water interface. There remains a need in the art for systems that can also prevent artifacts caused by the sample substrate. Furthermore, there is a need in the art for systems that are versatile and may be readily implemented for a diverse range of molecular targets, including proteins, organelles, single-cell organisms, and other types of targets.

SUMMARY OF THE INVENTION

The scope of the invention encompasses a number of novel innovations that enable the preparation of high quality cryo-EM samples. The novel methods, systems, and compositions of the invention are versatile and may be implemented for diverse sample types.

In a first aspect, the scope of the invention encompasses a novel method for sample preparation comprising the functionalization of sample grids with single-layer graphene oxide films. Described herein are methods for the efficient and facile deposition of high-quality graphene oxide films across a substantial portion of the sample grid surface.

In another aspect, the scope of the invention encompasses methods of functionalizing graphene oxide films with a variety of chemistries for the immobilization of a diverse array of target species. The various methods of the invention encompass functionalization of graphene oxide films with chemical and biological moieties that enable facile conjugation with diverse target species, including proteins, nucleic acids, organelles, cells, and other species of diverse size and composition.

In another aspect, the scope of the invention encompasses novel cryo-EM grids, which can be configured for conjugation with an infinite number of target species, and which facilitate concentration of the sample on the grid. In some implementations, the grids are general affinity grids, which capture target species by non-specific physiochemical interactions. In other implementations, the grids are functionalized with capture agents that can bind target species which have been functionalized with complementary binding partners. In some implementations, the novel functionalized grids of the invention are advantageously capable of long-term storage in a dried state at room temperatures, enabling mass production and affordable shipping to end-users for use with any number of sample types.

In another aspect, the scope of the invention encompasses the novel use of spacer moieties for optimal positioning of samples. The spacer moieties of the invention may include polyethylene glycol linkers that position samples at an optimal distance from the confounding influences of the sample substrate below and the air-water interface above. Furthermore, prior art systems tend to concentrate samples in a predominant orientation that limits the scope of data attained by cryo-EM imaging. In contrast, by the novel use of the polyethylene glycol linkers of the invention, the sample is presented at diverse orientations, enabling a rich analysis of samples at numerous angles for full resolution of structures.

The aforementioned methods, systems, and compositions provide the art with novel tools for fast and efficient preparation of high-quality samples, for a diverse variety of sample types, as next described in greater detail.

BRIEF DESCRIPTION OF THE DRAWINGS

FIGS. 1A and 1B depict a method of coating EM sample grids with high quality GO films. FIG. 1A: in the method of the invention, a support 105 is placed in a vessel 101. A cryo-EM grid 103 rests on the surface of the support. The grid comprises a perforated carbon film comprising a plurality of holes 104. The vessel is filled with liquid 109, such as water. A layer of multiple graphene sheets 106 is formed on the surface 102 of the water by adding a drop of solution comprising graphene sheets in a carrier. The liquid is then pumped from the vessel by a tube 107. FIG. 1B: The liquid 109 has been pumped out to the point that the surface 102 is below the Cryo-EM grid 103 resting on the support 104. A thin film of graphene oxide sheets 108 has coalesced and formed on top of the cryo-EM grid 103, covering the holes 104.

FIGS. 2A and 2B. FIG. 2A depicts a volume of water 201 having a top surface 203. Floating on the water are multiple graphene oxide sheets 202. Cryo-EM grids 205 sit upon a support 204, submerged in the water. FIG. 2B depicts a top view of the system wherein the graphene sheets are confined to a droplet 206 of carrier sitting on the surface of the water 203 by surface tension effects (arrows).

FIGS. 3A, 3B, 3C, and 3D. FIGS. 3A, 3B, 3C, and 3D depict a sample application and blotting method. FIG. 3A: Side view diagram of an inverted Cryo-EM grid comprising a perforated carbon layer 301, comprising multiple holes 302, on a metal grid comprising bars 307. The carbon layer 301 is coated with graphene oxide film 303. FIG. 3B: A droplet of solution 304 comprising sample proteins or other specimens 305 is applied to the back of the sample grid. Some of the sample molecules 305 adhere to the graphene oxide layer at the exposed holes 302. FIG. 3C: Filter paper 306 is applied to absorb liquid 304, and is kept from contacting the graphene film by the bars 307. FIG. 3D: After blotting, samples are adhered to the graphene oxide at the holes and only a thin layer of liquid 304 remains.

FIG. 4. FIG. 4 depicts sample concentration on a grid functionalized with capture agents. A perforated carbon grid 401 comprising a plurality of holes 402 is functionalized with a graphene oxide film 403. The graphene oxide film is functionalized with a plurality of constructs, each construct comprising a PEG chain 404, a functional moiety 405, for binding of capture agents, and a bound capture agent 406. The grid is exposed to a solution comprising a plurality of tagged target species 407. Tags on the target react with the complementary capture agents, forming covalent bonds 408.

FIGS. 5A, 5B, 5C, 5D, 5E, 5F, 5G, and 5H. FIGS. 5A, 5B, 5C, 5D, 5E, 5F, 5G, and 5H depict various chemical functionalization routes. FIG. 5A: a sample grid is functionalized with a film of graphene oxide sheets. FIG. 5B: By epoxy groups present on the graphene oxide film, reaction with a diamine results in an amine-functionalized grid. FIG. 5C. By epoxy groups present on the graphene oxide film, reaction with a diamine comprising a primary and a secondary amine results in a secondary amine-functionalized grid. FIG. 5D: By epoxy groups present on the graphene oxide film, reaction with an amine-PEG-azide construct results in an azide-functionalized grid, the azide separated from the graphene oxide by the PEG chain. Further reaction with an amine-PEG-maleimide construct results in a maleimide functionalized film, the maleimide separated from the graphene oxide by a PEG chain. FIG. 5E: A maleimide functionalized grid is reacted with a SpyTag peptide forming a SpyTag functionalized grid. When exposed to a tagged sample comprising a protein of interest fused to SpyCatcher protein, reaction between the SpyTag and SpyCatcher binds the sample covalently to the grid. FIG. 5F: A maleimide functionalized grid is reacted with a SpyCatcher protein forming a SpyCatcher-functionalized grid. When exposed to a tagged sample comprising a protein of interest fused to SpyTag peptide, reaction between the Spy Tag and Spy Catcher binds the sample covalently to the grid. 5G: An amine-nucleic acid construct is reacted with the grid, functionalizing it with a single stranded DNA molecule. 5H: The single stranded DNA-functionalized grid is reacted with a double stranded DNA sequence comprising single stranded overhang for hybridization with the functional group on the grid. The resulting double-stranded DNA functionalized sequence is able to bind DNA binding proteins that bind the selected sequence.

FIG. 6 depicts the position of TRAP1 proteins captured by an affinity grid. SpyTag was anchored to GO grid via a PEG spacer (M.W. 5000 Da) and SpyCatcher was fused to TRAP1 protein. A solution of Spy Catcher-TRAP1 fusion protein was exposed to the grid, with many Spy Catcher-TRAP1 fusion proteins immobilized on the grid. Subsequence freezing in liquid ethane produced a layer of ice and trapped particles. When analyzed by tomographic analysis, ice thickness was about 80 nm, with TRAP 1 particles located an average of 11.4 nm above the graphene oxide film and an average of 69 nm below the top surface of the ice.

FIG. 7A depicts an amino functionalized grid comprising a perforated sample grid coated with a layer of graphene oxide. By reaction of epoxide groups on the graphene oxide with ethyldiamine, the grid becomes functionalized with primary amines.

FIG. 7B depicts an amino functionalized grid comprising a perforated sample grid coated with a layer of graphene oxide. By reaction of epoxide groups on the graphene oxide with an amine-PEG-amine construct, the grid becomes functionalized with primary amines isolated from the graphene oxide surface by the PEG chain.

DETAILED DESCRIPTION OF THE INVENTION

Figure 1B:
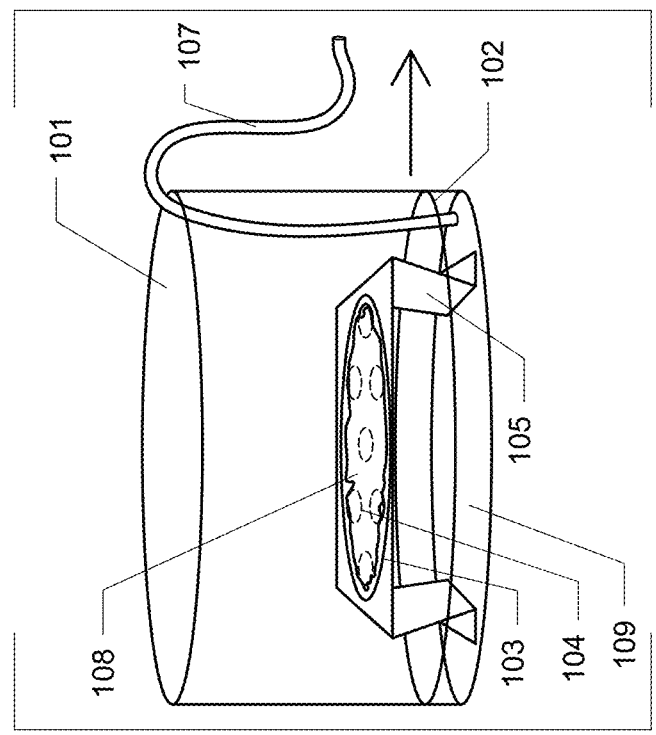
FIGS. 1A and 1B.
Figure 1A:
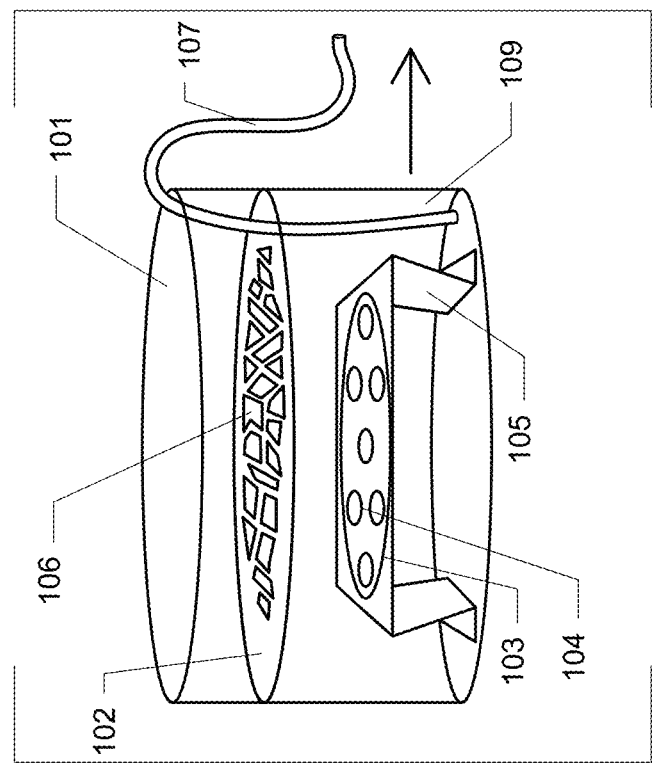
Figure 5E:
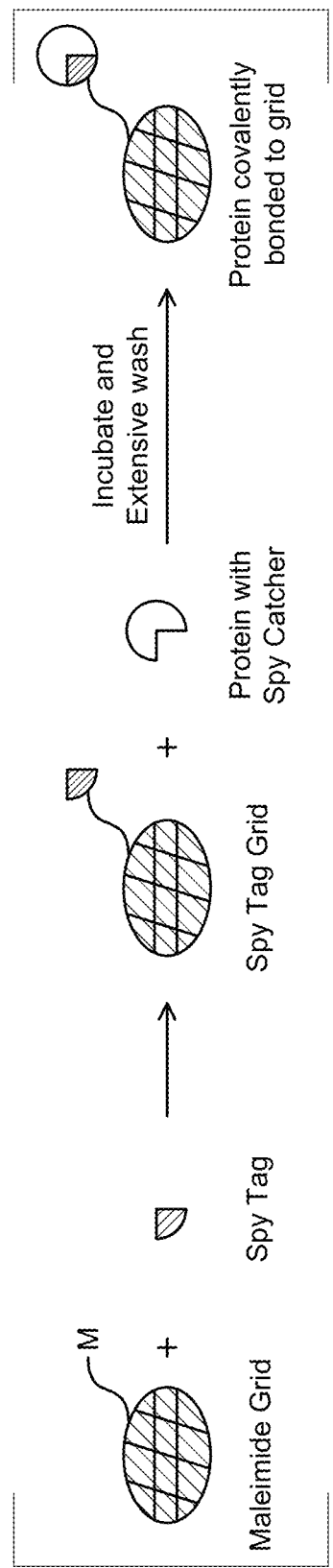
Figure 5F:
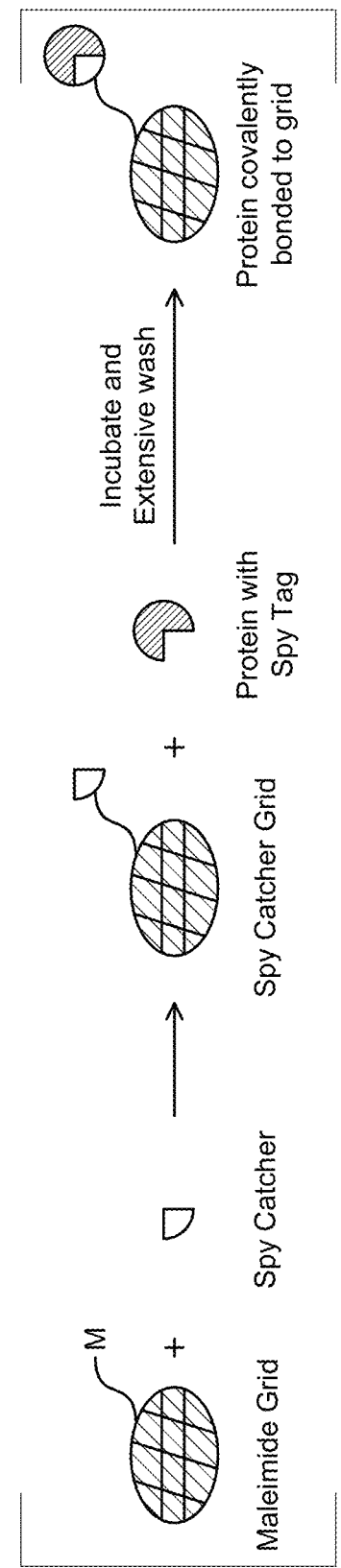
Figure 5G:
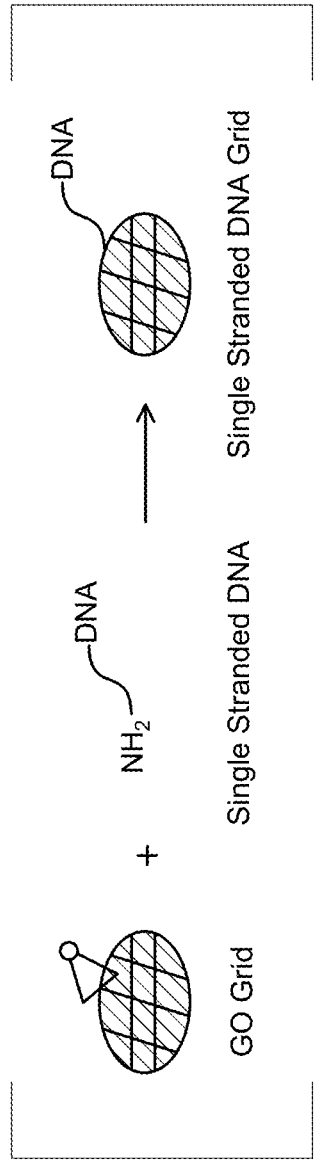
Figure 5H:
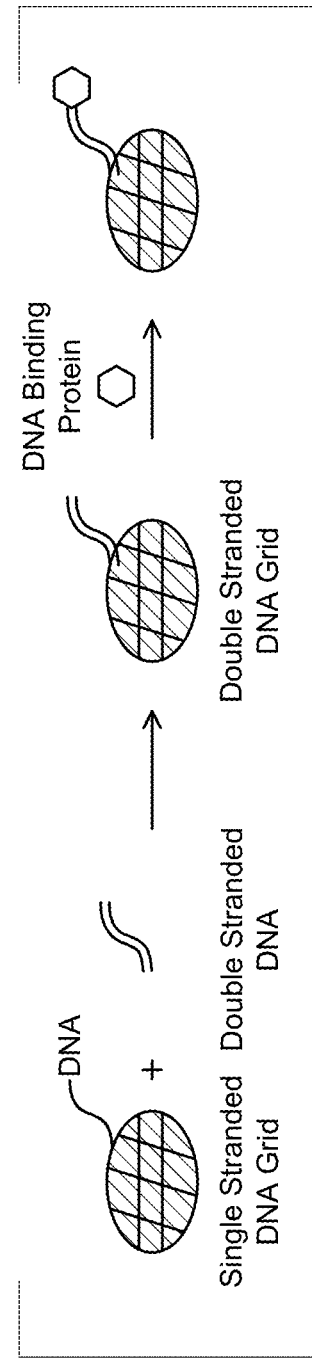

The scope of the invention encompasses various implementations, including novel types of affinity grids and methods of making them. The various elements of the affinity grid system are described next.

Substrate. In a primary implementation, the affinity grids of the invention are cryo-EM grids, i.e. holey grids for capturing specimens in ice for imaging by EM imaging modalities. These will be referred to herein as "grids" or "substrates." In a primary implementation, the substrate is a holey or perforated EM sample grid, as known in the art. The substrate may comprise any material known in the art, for example, in various embodiments, being carbon, including amorphous carbon, gold, including gold-coated materials, and silicon nitride, and other materials used in EM sample grids. Copper may be used in some implementations, but may be less than optimal for functionalization. Substrates may comprise bodies of any shape and size, for example, disks or squares. In a primary implementation, the substrate comprises a standard EM circular grid of 3 mm in diameter.

The substrate may be configured as a holey substrate, i.e. a planar structure perforated with a plurality of holes, or may comprise a mesh. The holes will generally have a regular spacing and average diameter. The holes may be circular, square, irregular, or any other shape. The holes may be arranged in a regular grid pattern or other pattern. The holes will have any diameter or width or spacing, for example, a diameter or width in the range of 1-5 µm.

Graphene Oxide Films. The substrates of the invention will be coated with a graphene oxide film. Graphene oxide enables quality functionalization with diverse chemistries. The graphene oxide film will preferably be single layer over a substantial percentage of the substrate and will span a substantial percentage of the holes of the grid.

The GO film may be applied to the substrate by any means known in the art. For example, grids may be coated with GO films by drop-casting methods. However, the quality of such GO films may be less than optimal. Previously reported drop casting methods may suffer from irregular coverage of GO sheets over the holes, with only a small percentage of holes covered by one or a few layers of GO sheets and the majority of the grids either covered with multi-sheet aggregates or lacking GO entirely.

Advantageously, presented herein is a novel method for GO coating of EM substrates that produces high quality coverage wherein a large percentage of holes are covered by single-sheet GO films ideal for functionalization, sample capture, and imaging.

In a first implementation, the scope of the invention encompasses a method of forming a sample-supporting film of graphene oxide on an EM substrate, comprising:

immersing the substrate in a solution contained in a vessel;

forming a thin film comprising graphene oxide sheets on the surface of the solution;

draining the solution from the vessel such that the substrate is deposited onto the substrate; and drying the substrate to adhere the film of graphene oxide sheets to the substrate.

The scope of the invention further encompasses a cyro-EM substrate coated with a graphene oxide film by the foregoing method.

In the coating method of the invention, the substrate is immersed in a solution. The solution may comprise any liquid capable of supporting a thin film of graphene sheets at the liquid-air interface. Preferred solutions are water and other hydrophilic compositions. In one embodiment, the solution has a high surface tension, for example being around or at least the surface tension of water. In one embodiment, the solution is pure water, for example, ultra-pure water.

The solution will be contained in a vessel. Any vessel type may be used, for example glass, polycarbonate, other materials). Exemplary vessels include petri dishes, crystallization dishes, culture wells, and beakers, for example, containing 10-50 ml (depending on the volume of the vessel) of water or other solution.

The substrate may be immersed under any depth of the solution for example, at least 0.5 cm from the solution surface. The substrate may rest on a support in the solution, for example, a coated metal support such as epoxy-coated stainless steel mesh or other corrosion resistant structure having holes or mesh to enable draining of solution.

A thin film of graphene oxide sheets is formed at the surface of the solution. The thin film may comprise any number of graphene oxide sheet layers, for example, an average of 1-5 sheets, for example, an average 1-3 graphene oxide sheets. It will be understood that the number of sheets will vary across the film, with aggregates in some places and thinner sections in others and the average represents a value such as the mean, median, or other quantification of the number of graphene oxide sheets found over a particular area.

Graphene oxide sheets will comprise discreet pieces of graphene oxide monolayer. The graphene oxide sheets will be present in pieces of a particular size range and size distribution. Preferred graphene oxide sheet sizes are in the range of 5-300 μm width, and may be substantially monodisperse or polydisperse.

The graphene oxide may comprise any density of oxygen groups, including epoxide bridges, carbonyl groups, hydroxyl groups, and phenol groups. The degree of oxidation can be tuned by chemistries known in the art, with varying densities of oxygen containing groups. Epoxy groups are especially favorable for functionalization reactions, and will preferably be present in sufficient abundance to provide functionalization sites at high densities. The oxidation level of graphene oxide can be roughly estimated from the carbon/oxygen (C/O) ratio, wherein higher values of the ratio means less oxidation. In one implementation, the GO films comprise a C/O ratio of about 1 to 3.5, for example values in the range of 1.3 to 2.5. In one implementation, the GO films will have a C/O ratio of 3.5 or less.

The film of graphene oxide sheets on the surface of the solution is formed by contacting the surface of the solution with a suspension of graphene oxide sheets dispersed in a carrier. The carrier may comprise any solvent known in the art, for example, an alcohol. The alcohol may comprise, for example, methanol, isopropanol, or any other volatile alcohol with low surface tension, for example, a surface tension lower than water. The graphene oxide sheets will be present at any concentration in the suspension, for example, in the range of 0.01-1.0 mg/ml.

A droplet of the GO and carrier, for example, having a volume of 0.001 to 1.0 ml, may be contacted with the surface of the solution. Upon contact, the solution will spread across the surface creating a film of 0.5-5.0 nm thick.

In another implementation, the film on the surface is compressed either manually or automatically to ensure that the graphene oxide sheets are in high concentration to provide good coverage, but not overlapping. One such means of accomplishing this is using a Langmuir Blodget tray.

Following the formation of a thin film of graphene oxide sheets on the surface of the solution, the solution in the vessel is drained, such that the thin film of graphene oxide sheets at the surface is lowered onto the substrate immersed in the solution. The solution may be drained by any means, for example, opening a hole in the bottom of the vessel or pumping the liquid from the bottom of the vessel by means of a pipette or pump. The speed of the draining process can be maintained within a desired range to facilitate even coating, for example, in the range of 0.01-3 ml/minute, for example, the surface dropping at a rate of 0.05-5.0 mm per minute. The means of removing the liquid should avoid bubbles, waves, or other perturbation of the surface such that an even film of graphene oxide sheets is maintained at the liquid-air interface.

As the liquid is drained from the vessel, the thin film of graphene oxide sheets will be deposited on the immersed substrate as it is exposed by the falling liquid level. Following this deposition, the thin film of graphene oxide sheets is adhered to the substrate by drying. Drying may be achieving passively by exposure to room temperature air of regular humidity (e.g. 20-25° C., relative humidity of 15-60%) for a period of 1-10 hours. Alternatively, active drying may be achieved by the application of moving air. Drying at room temperature is preferred.

In an alternative implementation, the support on which the substrates are resting is slowly raised above the surface of the solution such that the film of graphene oxide sheets is deposited on the substrate as it passes through the air-liquid interface.

The resulting films of graphene oxide will have superior quality and coverage. A quality graphene oxide support film will comprise a film wherein high-contrast multi-sheet aggregates are minimized. With regards to quality, in one embodiment, film area comprising a sheet thickness of 5 or less layers is considered usable. The film produced by the method of the invention may comprise 5 or less layers over at least 50%, at least 60%, at least 70%, at least 80%, or at least 90% of the substrate. In one embodiment, the film produced by the method of the invention will comprise 5 or less layers over at least 50%, at least 60%, at least 70%, at least 80%, or at least 90% of the hole area of substrate, hole area being the area of holes or openings in the substrate wherein sample particles are imaged. In one embodiment, films area comprising a sheet thickness of 3 or less layers is considered usable. The film produced by the method of the invention may comprise 3 or less layers over at least 50%, at least 60%, at least 70%, at least 80%, or at least 90% of the area of the substrate. In one embodiment, the film produced by the method of the invention will comprise 3 or less layers over at least 50%, at least 60%, at least 70%, at least 80%, at least 90%, or at least 95% of the hole space area of substrate. With regards to coverage, the coverage of the films produced by the methods of the invention will cover at least 50%, at least 60%, at least 70%, at least 80%, or at least 90% of the area of the substrate. The hole coverage of the films produced by the methods of the invention will cover at least 50%, at least 60%, at least 70%, at least 80%, at least 90%, or at least 95% of the hole area of the substrate.

For example, in the process described in the Examples below, overall coverage of graphene oxide sheet is over 95%. In covered areas, around 40% is single layer sheet, 40% is double layered sheet and the rest is triple layered sheet. Sheets with 4 or more overlapping layers are very rare.

In one aspect, the scope of the invention encompasses a cryo-EM sample grid coated with graphene oxide support films made by the methods described herein.

Functionalization of the graphene oxide support films. The graphene oxide support films of the invention may be functionalized with what will be referred to herein as "affinity moieties." An affinity moiety is a composition of matter that will immobilize and concentrate sample molecules or structures such as proteins, nucleic acids, organelles, viruses, cells other biological molecules. The Cryo-EM grids of the invention encompass any GO-coated sample substrate wherein the GO film is functionalized with a plurality of affinity moieties.

Non-Specific Affinity Moieties. In one implementation, the affinity moieties may comprise compositions that capture and concentrate target specimens by non-specific physiochemical interactions. Such nonspecific interactions may include charge. For example, in one embodiment, cryo-EM grid is functionalized with a positively charged affinity group that attracts target molecules having a net negative charge. In one embodiment, the cryo-EM grid is functionalized with a negatively charged affinity group attracting target molecules having a net positive charge. In another implementation, hydrophilic affinity groups are used, for attracting hydrophilic target molecules. In another implementation, the affinity group attracts target molecules by hydrogen bond forces. For example, affinity groups comprising hydrogen bond donors or hydrogen bond acceptors may be used. In one implementation, the affinity group comprises hydrogen atoms covalently bonded to electronegative atoms such as oxygen, fluorine, or nitrogen, creating a hydrogen-bond donating species, which may attract target species comprising hydrogen acceptors by hydrogen binding.

In one implementation, the non-specific affinity group is an amine. Amines may be used to attract and concentrate target species such as proteins. The positive charges of the amine groups provide general affinity for proteins and other sample molecules or moieties. Furthermore, the positive charges of the amine functional groups facilitate robust ice formation. In one implementation, the scope of the invention encompasses a cryo-EM sample grid (e.g. holey or mesh type grid) coated with GO wherein the GO is functionalized with a plurality of amine groups. In one embodiment, the amine groups are primary amines. In one embodiment, the amines are secondary amines.

In one implementation, the affinity moiety comprises a composition that selectively binds one or more target species. The use of affinity moieties having high affinity and selectivity for complementary targets enables efficient concentration and simultaneous purification of target species "on the grid."

In one implementation, the affinity moiety is an antibody or antigen binding fragment thereof which binds to a target protein or other specimen with high specificity. In another embodiment, the capture agent is a ligand, or a receptor or binding domain thereof specific for a particular target or class of targets, for example, comprising a receptor, protein extracellular domain, antibody, nanobody, Fab, single chain antibody, or other species that binds a complementary moiety on the target specimen with high affinity.

In another implementation, the functional group of the modifying moiety comprises a nucleic acid sequence. For example, the nucleic acid sequence may comprise DNA, RNA, PNA, or other natural or non-natural nucleic acid compositions known in the art. In one embodiment, the affinity moiety comprises a morphalino oligonucleotide. In one embodiment, the nucleic acid is single-stranded DNA. In one embodiment, the affinity moiety comprises double-stranded nucleic acid. The nucleic acid functionalized grids of the invention may be used to capture DNA-binding specimens. The nucleic acid sequence may be selected for capture of DNA-binding proteins or other specimens (e.g. transcription factors) by sequence-specific interactions. In one embodiment, the specimen comprises a DNA binding protein. In some embodiments, the specimen comprises a composition comprising, for example functionalized with, nucleic acid sequences complementary to the affinity group. In an alternative implementation the nucleic acid affinity group captures target specimens by non-specific interactions (e.g. for nonspecific DNA binding proteins such as histones).

In other implementations, the capture agent comprises one member of a generic tagging system pair. Tagging systems comprise a first and a second binding partner that, under suitable conditions, often with the aid of a specific enzyme of the tagging system (e.g. a ligase), form covalent bonds to each other with high affinity. In various embodiments, the scope of the invention encompasses a GO-coated cryo-EM substrate functionalized with one binding partner of a selected tagging system. In this implementation, the substrate is functionalized with a capture agent comprising the first binding partner of the selected tagging system pair and the specimen is modified with the second, complementary binding partner of the selected tagging system pair, such that, when presented to the functionalized substrate under suitable conditions, the specimen is bound to the substrate by the interactions of the complementary binding partners.

For example, in the case of a target specimen comprising a protein, the target protein may be engineered and expressed as a fusion protein comprising a tagging system binding partner peptide or protein that is complementary to the tagging system partner which the cryo-EM substrate is functionalized with. For example, fusion addition of the tagging system binding partner peptide or protein at the C- or N-terminus of the target protein may be achieved. In alternative implementations, the samples are modified by the addition of the selected peptide or protein binding partner by chemical ligation techniques known in the art.

In one embodiment, the selected tagging system is the SpyCatcher-SpyTag system, as known in the art. As used herein, reference to SpyCatcher and SpyTag compositions includes the SpyTag sequence of SEQ ID NO: 1; the SpyCatcher sequence of SEQ ID NO: 2; compositions described in U.S. Pat. No. 9,547,003, entitled "Peptide tag systems that spontaneously form an irreversible link to protein partners via isopeptide bonds," by Howarth; improved forms of SpyCatcher and SpyTag known in the art, and variants of any of the foregoing. As used herein, reference to the "variant" of a peptide or protein means: a truncated version which retains some level of activity of the original sequence; a sequence comprising additions to the enumerated sequence which retains some level of activity of the original sequence; and/or an amino acid sequence having at least 75%, at least 80%, at least 85%, at least 90%, at least 95%, or at least 99% sequence identity to the enumerated sequence and which retains some level of activity of the original sequence.

In one embodiment, the scope of the invention encompasses a GO-coated cryo-EM substrate functionalized with a SpyCatcher protein. In one embodiment, the SpyCatcher protein is SEQ ID NO: 2 or a variant thereof. In an alternative implementation, the scope of the invention encompasses a GO-coated cryo-EM substrate functionalized with a SpyTag peptide. In one embodiment, the SpyTag peptide is SEQ ID NO: 4 or a variant thereof. Meanwhile, in the use of such grids, the target specimen comprises or is modified with the complementary binding partner of the tagging system. For example, in one embodiment, the target species is modified with SpyTag, for capture by an affinity grid functionalized with SpyCatcher protein. Conversely, the target protein comprise or be modified with the SpyCatcher protein, for capture by an affinity grid functionalized with SpyTag peptide. Advantageously, SpyTag functionalized cryo-EM substrates may be stored for long periods of time under dry conditions at ambient temperatures. Such SpyTag functionalized cryo-EM substrate thus provide a convenient system for storage, shipping, and end-use.

In one embodiment, the selected tagging system is the SnoopCatcher-SnoopTag system, as known in the art. As used herein, reference to SnoopCatcher-SnoopTag compositions includes the SnoopCatcher sequence of SEQ ID NO: 3; the SnoopTag sequence of SEQ ID NO: 4; compositions described in Veggiani et al. Programmable polyproteams built using twin peptide superglues. *Proc Natl Acad Sci USA* 2016, 113, 1202-1207; improved forms of SnoopCatcher and SnoopTag known in the art, and variants of any of the foregoing.

In one embodiment, the scope of the invention encompasses a GO-coated cryo-EM substrate functionalized with a SnoopCatcher protein. In one embodiment, the SnoopCatcher protein is SEQ ID NO: 3 or a variant thereof. In an alternative implementation, the scope of the invention encompasses a GO-coated cryo-EM substrate functionalized with a SnoopTag peptide. In one embodiment, the SnoopTag peptide is SEQ ID NO: 4 or a variant thereof. Meanwhile, in the use of such grids, target specimen comprises or is modified with the complementary binding partner of the tagging system. For example, in one embodiment, the target species is modified with SnoopTag, for capture by an affinity grid functionalized with SnoopCatcher protein. Conversely, the target protein comprises or is modified with the SnoopCatcher protein, for capture by an affinity grid functionalized with SnoopTag.

In one embodiment, the selected tagging system is a HaloTag tagging system, as known in the art. As used herein, reference to HaloTag system compositions includes the HaloTag sequence of SEQ ID NO: 5; chloroalkane ligands such as $(CH_2)_{2-3}X$ where X is a halide and a functional group such as carboxytetramethylrhodamine, e.g., carboxytetramethylrhodamine-$C_{10}H_{21}NO_2$—C; compositions described in U.S. Pat. No. 7,425,436, entitled "Covalent tethering of functional groups to proteins and substrates therefor," by Darzins et al; compositions described in Los et al. HatoTag: A novel protein labeling technology for cell imaging and protein analysis. *Acs Chem Biol* 3, 373-382 (2008); improved forms of Halo Tag and its chloroalkane ligands known in the art, and variants of any of the foregoing.

In one embodiment, the scope of the invention encompasses a GO-coated cryo-EM substrate functionalized with a Halo Tag protein. In one embodiment, the Halo Tag protein is SEQ ID NO: 5 or a variant thereof. In an alternative implementation, the scope of the invention encompasses a GO-coated cryo-EM substrate functionalized with a chloroalkane ligand suitable for capture by a HaloTag protein, for example, by a HaloTag protein of SEQ ID NO: 5. Meanwhile, in the use of such grids, the target specimen comprises or is modified with the complementary binding partner of the tagging system. For example, in one embodiment, the target species is modified with a chloroalkane ligand, for capture by an affinity grid functionalized with HaloTag protein. Conversely, the target protein may comprise or be modified with the HaloTag protein, for capture by an affinity grid functionalized with a suitable chloroalkane ligand.

Other tagging systems may be utilized, wherein, the scope of the invention encompasses a GO-coated cryo-EM substrate functionalized with one binding partner of a tagging system selected from: a split GFP tagging system, for example, as described in Chalfie et al. Green fluorescent protein as a marker for gene expression, *Science*. 1994 Feb. 11; 263 (5148): 802-5; the DogTag tagging system; the Isopeptag tagging system; the SdyTag tagging system; biotin-avidin tagging systems; strepavidin-biotin tagging systems; and polyhistidine tagging systems, as known in the art.

Intervening Spacers. In some implementations, the affinity group is conjugated directly to the GO surface, or is joined thereto by a minimal composition. However, in a primary implementation, the modifying group will comprise a substantial intervening spacer chain. The function of the intervening spacer is to physically and/or chemically isolate proteins or other specimens from the GO surface. It has previously been shown that interactions between the specimen and the substrate can alter the quality of the specimen, for example, distorting the molecule, chemically altering the molecule, or resulting in a preferred orientation that limits the ability to resolve the specimen from all aspects. Accordingly, in many cases it is preferable to utilize a spacer or linker macromolecule that removes the captured specimen from the grid, effectively passivating the substrate.

In various embodiments, the scope of the invention encompasses a GO-coated cryo-EM substrate functionalized with an affinity group, wherein the affinity group is joined to the GO surface by a construct comprising an intervening spacer.

The intervening spacer may comprise any chemical composition. In one embodiment, the intervening spacer composition is a polymeric composition of matter. In one embodiment, the polymer is an alkyl chain. In one embodiment, the polymer is a polyethylene, a polyester, a polyether, or polyalcohol. In one embodiment, the polymer comprises poly(N-isopropylacrylamide) (PNIPAM). In one embodiment, the intervening spacer is polyacrylamide (PAM). In one embodiment, the intervening spacer is poly(acrylic acid). In one embodiment, the intervening spacer is polymethacrylate or another acrylic polymer. The intervening spacer may be of any size, for example, in the range of 100 to 10,000 Daltons, for example, 500-5,000 Daltons. Exemplary intervening compositions include PEG polymers having average molecular weights of 100, 500, 600, 750, 1,000, 2,000, 3,0000, 4,000, 5,000, 6,000, 7,000, 8,000, 9,000, and 10,000 Daltons In a primary embodiment, the polymer is polyethylene glycol (PEG). As demonstrated herein, PEG moieties impart several advantages, including passivation of the substrate, improved wetting and ice formation on the substrate, and presentation of the specimen at diverse orientations. PEG chains of any length may be utilized, for example, PEG of average molecular weight in the range of 100 to 10,000 Daltons, for example, 500-5,000 Daltons. Exemplary intervening compositions include PEG polymers having average molecular weights of 100, 500, 600, 750, 1,000, 2,000, 3,0000, 4,000, 5,000, 6,000, 7,000, 8,000, 9,000, and 10,000 Daltons.

Methods of Functionalizing GO-Coated Cryo-EM Substrates. The cryo-EM sample grids of the invention may be functionalized by any means. Functionalization requires modification of the GO surface with groups suitable for the conjugation of affinity groups or capture agents. The GO films of the invention are amenable to modification by any number of diverse chemistries.

In one implementation, functionalization of the GO film is achieved by exposing the GO-film coated to a modification moiety under suitable conditions for attachment of the modification moiety to the GO film. The modification moiety is a composition of matter comprising:

A-B-C, wherein:

A is a reactive moiety that will react to one or more chemical groups present on the GO-film such that the modification moiety is bound, adsorbed, conjugated, or otherwise attached to the GO film;

B is an optional intervening spacer composition, which may have any number of compositions, as described above; and C is a functional moiety that is presented by the modified GO film after completion of the modification reaction or reactions. In some implementations, C is an affinity moiety. In other implementations, the functional moiety C may be further modified by the addition of molecules or other reactions for the addition of affinity moieties.

The reactive moiety A may be any chemical entity that, under suitable conditions, by one or more reactions, attaches the modifying moiety to the GO film. In one implementation, the modifying moiety comprises a chemical entity that binds to the GO film at epoxide groups of the GO film, for example, via nucleophilic reaction. In one embodiment the modifying moiety comprises a chemical entity that functionalizes carboxyl groups of the GO film, although these are generally less abundant than the epoxy groups and are present mostly at the edges of GO sheets. In one embodiment, the modifying moiety comprises a chemical entity that functionalizes both epoxy and carboxyl groups of the GO sheets. In one embodiment, the modifying moiety comprises a chemical entity that functionalizes groups other than epoxy or carboxyl groups of the GO sheets.

In one embodiment, the reactive moiety, A, of the modifying moiety comprises an amine. In one embodiment, the amine reacts with epoxy groups of he GO film by nucleophilic ring opening reactions, for example, under nonaqueous conditions. In one embodiment, the reactive group of the modifying moiety is a primary amine. In one embodiment, the reactive moiety comprises a secondary amine. In one embodiment, the reactive moiety comprises a tertiary amine. The modifying molecule comprising an amine may be introduced to the grid in nonaqueous solution, for example in dimethyl sulfoxide (DMSO), for example, DMSO at a concentration of 10 mM.

In alternative implementations, the reactive moiety comprises other chemical compositions that are reactive with epoxy, for example, a hydroxyl, thiol, phenol, or anhydride composition.

Regarding the intervening composition, in some implementations, the modifying moiety does not comprise an intervening composition, or comprises a minimal intervening chemical entity. In such cases, the modifying moiety basically comprises a reactive group conjugated to the functional group, for example, an ethylenediamine, or N-Methyl-1,3-diaminopropane.

In various implementations, the functional moiety, C, of the modifying moiety, also comprises an amine. In one embodiment, the functional moiety is a primary amine. In one embodiment, the functional moiety comprises a secondary amine. In one embodiment, the functional moiety comprises a tertiary amine.

In some implementations, both the reactive moiety and the functional moiety of the modifying moiety comprise and amine, such that the modifying moiety is a diamine. Preferably, the diamine modifying moiety comprises two identical amines, i.e. two primary amines, two secondary amines, or two tertiary amines of the same type. However, it will be understood that heterodiamine modifying moieties are within the scope of the invention. In one embodiment, the diamine is ethylenediamine. In one embodiment, the diamine comprises an intervening spacer composition, for example PEG. Following modification of the GO film with a diamine modifying molecule, the grid will comprise a GO film functionalized with amines.

In one embodiment, the modifying moiety comprises an amine reactive group and a nucleic acid functional group, such that the GO film coated grid is functionalized with the nucleic acid by amine-epoxy reactions. Single-stranded nucleic acid functional groups may be converted to double stranded nucleic acid functional groups by hybridization with nucleic acids comprising complementary strands under suitable conditions.

In other implementations, the functional moiety comprises an alkyne. In some implementations, the reactive moiety comprises an amine and the functional moiety comprises an alkyne. For example, in one embodiment, the modifying moiety comprises an amino-alkyl composition or dibenzocyclooctynes-PEG-amine. When the GO film is functionalized with such groups, the end-product is an alkyne-functionalized GO film-coated grid. Such alkyne-functionalized grids may be reacted with additional modifying compositions for the addition of different functional groups. For example, the alkyne-modified grid may be functionalized by alkyl-azide cycloaddition, e.g. click chemistry reactions, wherein a secondary molecule comprising an azide group a secondary functional moiety is reacted with the alkyne-modified grid. In another implementation the positions of the alkyne and azide are reversed, with the functional moiety of the modifying moiety comprising an amino-azide composition, for example, an amino-PEG-azide composition. Subsequent reaction with an affinity group conjugated to an alkyl group can be used to functionalize the substrate with the affinity group.

In one embodiment, the alkyne-modified GO-film coated grid is functionalized with maleimide. The maleimide may be conjugated with an azide group, and is added to the alkyne group by reaction with the alkyne-modified GO-film coated grid under suitable conditions for alkyne-azide conjugation. The end product of such reaction is a grid functionalized with maleimide groups. The maleimide groups may be further reacted, by conjugation chemistries known in the art, with proteins. For example, proteins comprising capture agents, as described below, may be conjugated to the maleimide. For example, a maleimide-modified GO film-coated grid may be functionalized with capture agents by sulfhydryl reactions between the maleimide functional groups and cysteine or methionine residues of a protein.

In other embodiments, the functional group may comprise any of carboxyl groups, hydroxyl groups, phenol groups or reactive groups such as NHS, or sulfo-NHS. These can be further reacted with affinity groups conjugated to compatible moieties for conjugation.

In some embodiments, the intervening composition is provided to the GO film in a secondary modifying molecule. For example, an alkyne-modified film may be prepared by use of a first modifying moiety, as described above, wherein the first modifying moiety optionally contains or lacks an intervening composition, such as PEG. The alkyne film may subsequently be functionalized with a secondary modifying moiety comprising an azide, an intervening composition, such as a PEG macromolecule, and a terminal maleimide.

Methods of Use. The scope of the invention further encompasses methods of using the affinity grids described in the foregoing section. The general method of the invention encompasses the steps of:
  exposing an affinity grid of the invention to a solution comprising a specimen, under conditions suitable for binding of the specimen to the affinity grid;
  blotting the grid to remove excess specimen solution;
  immersing the grid in a freezing solution to form amorphous vitreous ice, wherein specimens are immobilized in the ice in a substantially hydrated condition; and
  imaging the grid by EM.

The specimen may comprise any composition of matter. In a primary implementation, the specimen is a protein. In other embodiments, the specimen is a small molecule, organelle, cell, virus, DNA origami, structured RNA or other chemical or biological composition. In some implementations, the specimen has been modified with a first binding partner of a tagging system, wherein the affinity grid is functionalized with the second, complementary binding partner of the tagging system.

Advantageously, by the efficient "concentration on the grid" of the affinity grids of the invention, the concentration of the specimen in the sample solution provided to the grid may be lower than that used in prior art specimen preparation methods. This enables the use of difficult-to-express proteins or dilute species present in complex biological samples. Furthermore, the use of lower concentrations of specimen avoids aggregation and other complications that result from the use of highly concentrated specimens. For example, in various implementations, the specimen is present in the sample solution at a concentration of less than 50 nM, less than 100 nM, less than 200 nM, less than 500 nM, less than 1 µM, less than 5 µM, or less than 10 µM.

In providing specimen to the GO-coated grids of the invention, in order to protect GO-bound proteins or other specimen types from possible deleterious filter paper interactions, sample may be applied to the back side of the grid. During blotting, the grid bars should help prevent the filter paper from directly contacting the GO-bound proteins. Relatively longer than standard blotting times may be used, for example, blotting times of 10-60 seconds, for example 25-35 seconds.

Affinity grids of the invention, and specimens provided therewith, for example, by the aforementioned preparation method, may be imaged by any EM imaging modality known in the art. As set forth in the Examples below, the high quality specimens provided by the affinity grids and associated methods of the invention enable the collection of high quality data for the structural resolution of diverse targets.

EXAMPLES

Example 1. General and Robust Covalently Linked Graphene Oxide Affinity Grids for High-Resolution Cryo-EM Here is presented a novel affinity grid approach that combines a small, essentially infinite affinity covalent tagging system with chemically derivatized graphene oxide (GO) support films only 1-2 molecules thick. Graphene oxide (GO) was selected as the supporting film because (i) it significantly reduces background compared to amorphous carbon, (ii) it is decorated with abundant oxygen-containing functional groups which facilitate further chemical modification, and (iii) is more straightforward to make and to coat grids than pure graphene crystals. To coat GO sheets onto EM grids, a revised method of Langmuir-Blodgett assembly, as described by Cote et al. was used. The GO water stock solution was diluted with methanol/water (5:1, v:v) to a concentration of 0.1 mg/ml. Mild stirring for 30 mins rather than sonication was used to avoid destruction of GO sheets, producing a GO working solution. An epoxy coated stainless steel mesh stand was placed at the bottom of a glass petri dish (60 mm in diameter, 15 mm in height) and DI water was filled to the top. EM grids (Au QUANTIFOIL™, 300 mesh) were used as received and placed on the mesh with carbon side facing upward. Then a total volume of 230 µl of GO working solution was spread dropwise onto the water surface at different spots at a speed of 50 µl/min using a syringe. After the water was drained, the GO coated grids were dried at room temperature overnight for use. Coverage of GO was examined by TEM with an acceleration voltage of 200 kV. Estimated GO coverage of the grid surface was over 90%, with ~40% being monolayer, 40% bilayer and less than 20% having three or more layers.

Figure 6:
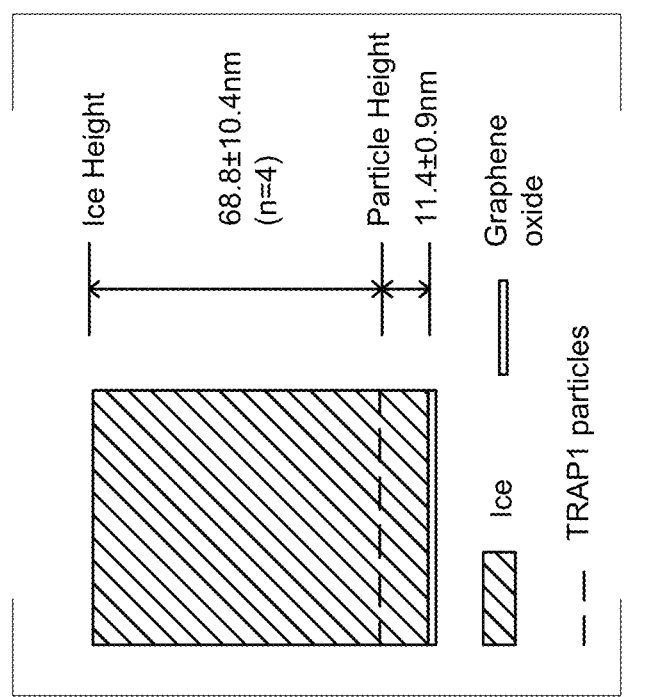
FIG. 6.

Considering that carboxyl groups mainly decorate on the edges of GO sheets, it was decided to use the epoxide groups that cover the bulk of planar area for functionalization. In order to reduce non-specific grid interactions and to position the sample away from the grid surface as well as the air-water interface, thereby avoiding potential sample denaturation or preferred orientation problems, a polyethylene glycol (PEG) spacer was used. PEG of molecular weights of 600 Da and 5,000 Da were tested. First, an amino-PEG-alkyne coupled linker was coupled to the grid, and then a target-specific reactive azide-PEG spacer was coupled in a second step using Cu-free click chemistry. As the GO-PEG-alkyne grids were quite stable, this allowed the use of a wide range of coupling chemistries/reactive groups to link the tag catcher to the grid. In the example here, an azide-PEG-maleimide modifying group was used to couple to a cysteine on the SpyTag or SpyCatcher to pre-formed PEG-alkyne grids. The presence of the PEG segment helped passivate the grid surface, rendered it sufficiently hydrophilic to vitrify well, spaced the target away from the surface and also increased the flexibility to minimize potential issues with preferential orientation. FIG. 6 depicts average particle height of TRAP1-SpyCatcher fusion proteins immobilized on a SpyTag functionalized grid with 5,000 Dalton PEG spacer, showing good positioning away from the GO surface and well below the air liquid interface above.

In a 1.5 ml centrifuge microtube, one GO coated EM grid (GO grids) was submerged in 20 µl of dibenzocyclooctyne-polyethylene glycol-amine (DBCO-PEG4-Amine) solution in dimethyl sulfoxide (DMSO) at a concentration of 10 mM and shaken at room temperature overnight. Following that, the DBCO functionalized grid was washed by DMSO and DI water for three times, respectively, and submerged in 20 µl of azide-polyethylene glycol-maleimide (M.W. 600 or M.W. 5000 Da, Nanocs PG2-AZML-5k) solution in DI water. The reaction was shaken at room for 6 hours and the grid was washed by DI water and ethanol for three times, respectively. The as-made maleimide grid was then dried in ambient for half an hour and stored at −20° C. for future use.

The self-ligating SpyCatcher/SpyTag coupling system forms a covalent bond between the ~14 KDa SpyCatcher and a 12 residue peptide, either of which can be fused to the protein of interest and the partner then coupled to the grid. The irreversible covalent bond forms within minutes and is highly specific and robust, paving the way for "purification on the grid". A buffer with a pH of 7.5 containing 20 mM HEPES, 60 mM KCl was used throughout the process. SpyCatcher was diluted with buffer to a final concentration of 1.4 µM. SpyTag peptide was first dissolved in DMSO to a concentration of 560 µM and then diluted with buffer to a final concentration of 2.8 µM. For affinity testing with SpyTag on grid, one maleimide grid was first incubated in 200 µl of SpyTag solution at room temperature for 2 hours. The grid was washed with DI water and ethanol 3 times, and dried in ambient for 1 hour. Then the grid was picked up by tweezers from VITROBOT™ IV (Fisher Thermo Scientific) and placed horizontally.

After coupling the SpyTag or SpyCatcher to the maleimide grids, incubation with a cognate-tagged protein of interest efficiently formed a stable attachment in a matter of minutes. In a first example, a SpyTag grid was exposed to a dilute solution (270 nM) of the dimeric mitochondrial Hsp90 molecular chaperone (TRAP1, ~150 KDa) fused to either SpyTag (control) or SpyCatcher (cognate sample, total molecular weight ~165 KDa). The grids were extensively washed to remove unbound or loosely adsorbed proteins. TRAP1 with SpyCatcher or SpyTag was diluted in buffer with 1 mM ADP-BeF$_x$/MgCl$_2$ and was incubated at 37° C. for 30 min to achieve a homogenous closed state of TRAP1[24]. The concentration of TRAP1 was 270 nM in all cases.

In ambient, 3 μl of solution of TRAP1 with SpyCatcher was applied to carbon side of the grid and incubated for 4 min. The grid was washed by flipping the grid downward and touching 30 μl of buffer droplet with carbon side on parafilm for three times. After each wash, liquid was drained by filter paper. Then 3 μl of solution of TRAP1 with SpyCatcher was applied to carbon side of the grid and incubated for another 4 min. The grid was washed with buffer using the same way mentioned above. Very quickly 3 μl of buffer was applied to the grid before it was completely dried. Tweezers with the grid was retracted to cryogenic chamber and blotted immediately using the following condition: 22° C., 100% humidity, blot force 1, blot time 8 s. Grid was plunged into liquid ethane and stored in liquid nitrogen. For the negative control, TRAP1 with SpyTag was applied instead to the grids.

A total of 5 cryo-EM datasets were collected. For the first dataset, TRAP1 fused with SpyCatcher was applied to GO grids functionalized with SpyTag and PEG spacer M.W. 5000 Da. A total of 2670 micrographs were collected using beam-image shift on an EM microscope operated at 300 kV with a direct electron detector and a slit width of 20 eV. Images were recorded with SERIALEM™ in super-resolution mode with a pixel size of 0.407 Å. Defocus varied from 0.8 μm to 2.5 μm. Each image was fractionated to 80 frames (0.1 sec each, total exposure of 8 seconds) with dose rate of 8.6 e/Å$^2$/sec for a total dose of 68.8 e/Å$^2$.

The other 4 datasets were collected on an EM microscope equipped with a K3 detector. The microscope was operated at 200 kV at a nominal magnification of either 36,000× or 28000×, corresponding to super-resolution pixel sizes of 0.57 Å/pix or 0.72 Å/pix. Defocus varied from 0.8 μm to 2.5 μm. Each image was fractionated to 100 frames (0.03 sec each, total exposure of 3 seconds) with dose rate of 24.7 e/Å$^2$/sec for a total dose of 74.1 e/Å$^2$.

Image stacks were motion corrected and summed using MotionCor2, resulting in Fourier-cropped summed images. CTFFIND4 was used to estimate defocus parameters for all the images. Initial particle picking was carried out without a template to generate the 2D class averages, which were then used as templates for a second-round particle picking on micrographs with 25 Å low-pass filtering. RELION 3.0 beta was used for all the following steps. Reference free 2D classification were performed for 25 iterations using images binned by 4. Bad particles were excluded based on 2D average results. The remaining particles were 3D classified into 10 classes using images binned by 2 and an initial model generated from the crystal structure of zebrafish TRAP1 and lowpass filtered to 50 Å. The particles from the 3D classes with high-resolution features were reextracted without binning and subjected to 3D auto-Refinement in Relion. The resulting maps from refinement were post-processed and sharpened by an automatically estimated B-factor in RELION. All resolutions were estimated by applying a soft mask around the protein density and the gold-standard Fourier shell correlation (FSC)=0.143 criterion.

In the non-cognate control sample, very few TRAP1 molecules were visible. By contrast, applying TRAP1-SpyCatcher to the same SpyTag affinity grids resulted in a very satisfactory particle density and is suitable for high resolution studies. This clearly demonstrates successful and specific affinity capture on the grid with the SpyCatcher/SpyTag system. Obtaining a similar particle density on a regular grid (QUANTIFOIL™ holey carbon gold grid, 300 mesh) required a concentration of ~2 μM, indicating the ability of the affinity grid to specifically concentrate the protein of interest. High-resolution features of TRAP1 were clearly viable in the 2D class averages and suggest the data collected are of high quality with minimal impact on contrast from grid modification.

In the current study, the human mitochondrial Hsp90 (TRAP1) was used as a test sample. It is much smaller (~150 kDa) than samples typically used for testing grid technologies, such as proteasomes and ribosomes, thus making it a stringent test of grid background, contrast, and achievable ice thickness. It also turned out to be particularly sensitive to partial denaturation at the air-water interface. Each TRAP1 protomer within the dimer consists of 3 individual domains: N-terminal domain (NTD), Middle domain (MD), and C-terminal domain (CTD). Together these domains go through a complex ATP binding and hydrolysis cycle that plays a key role in regulating mitochondrial protein homeostasis and function. Although the crystal structure of TRAP1 from zebrafish had been determined previously, human TRAP1 has proven to be a significant challenge for both X-ray crystallography (producing only poorly diffracting crystals) and cryo-EM. Despite being able to collect a large, high quality dataset, previous attempts of solving the human TRAP1 cryo-EM structure using standard grids produced predominantly a structure where only the TRAP1 NTD and MD from each protomer were resolved. Notably, this structure is different from a reported crystal structure of TRAP1 in which the CTDs were proteolyzed and crystallized post closure. Only a minor population of particles representing full-length TRAP1 could be classified in 3D resulting in a medium resolution reconstruction even when starting with a large dataset. The dimerization interface between the NTDs of each protomer is preserved in the dominant structure, which only happens when starting with full length protein. Thus, the disruption of the CTD dimerization interface most likely occurs upon grid preparation, presumably due to the interaction with the air-water interface, resulting in a flexible or denatured CTD invisible in the reconstructions.

The GO based affinity grids demonstrated herein solved this problem, and full-length particles were easily visible in the raw micrographs as well as in the 2D class averages. It is hypothesized that the preservation of the TRAP1 CTD dimerization interface is due to the affinity tags keeping the protein away from the air-water interface. As demonstrated by tomography, the PEG spacer kept the protein away from both the air-water interface and the GO surface, thereby avoiding potentially unfavorable interactions with regions of unmodified GO. Although the TRAP1 dimer state missing the CTD density was still present in the affinity grid dataset (reconstructed to 3.1 Å resolution), the ratio between full-length TRAP1 population and CTD missing population was improved from 1:6.5 to 1:2.3 after discarding low quality particles through 3D classification. Thus, by the affinity grids, the full-length TRAP1 structure was resolved at 3.3 Å resolution. This structure closely resembled the reported crystal structure of zebrafish TRAP1 and exhibited the same pronounced asymmetry, proving that this distinctive conformation is both conserved across species and that it is not a consequence of crystallization. Having datasets for the same sample using both conventional grids and the affinity grids revealed clear differences in orientation bias. From the 2D averages, side views were quite rare with conventional grids, but prevalent with the affinity grids.

To further evaluate the SpyCatcher/SpyTag affinity grid, the test was also performed in the reverse manner, immobilizing SpyCatcher on the grid, and then applying TRAP1-SpyTag. two different PEG chain lengths were tested (600 Da vs 5000 Da M.W.) in the azide-PEG-maleimide spacer. While full reconstructions was not pursued in these cases, there were no apparent differences in either particle density or 2D class average quality.

In summary, the GO based affinity grids provided selective enrichment of a tagged sample on the grid without negatively impacting image contrast and particle orientation. This allowed even small particles to be readily reconstructed at high-resolution. Furthermore, the ability of the affinity grids to protect delicate samples from partial denaturation/aggregation at the air-water interface was demonstrated. In this example, the full-length structure of human TRAP1 at atomic resolution was performed for the first time, paving the way for future structure-based drug discovery experiments.

Example 2. Surface Functionalized Graphene Oxide Coated Grid Provides General Affinity for Cryo-Electron Microscopy Here is demonstrated a novel and convenient approach featuring chemical modification of graphene oxide (GO) coated grids. Grids are evenly covered with GO bearing amino groups on the surface after functionalization. Testing of four different samples on these grids shows that 1) proteins were enriched, 2) particle distribution was improved over the holes of the substrate, and 3) particle orientations were changed. Using the 20S proteasome, cryo-electron tomography experiments were conducted and confirmed that particles stay close to the GO surface other than the air-water interface on the GO-amino grids. Moreover, a polyethylene glycol (PEG) spacer was added between the amino group and the GO surface to make a GO-PEG-amino grid which kept particles away from both the GO surface and the air-water interface.

Figure 7A:
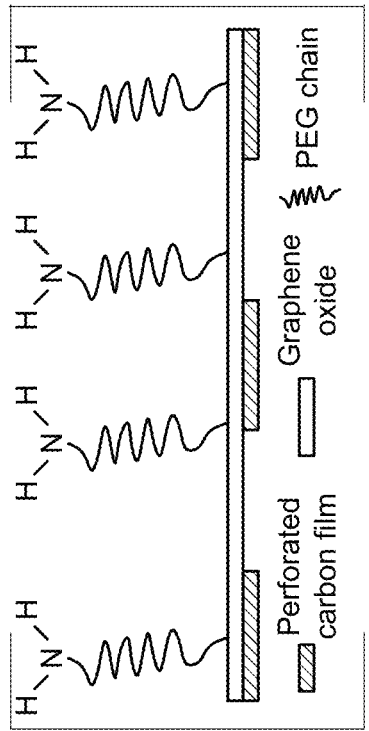
FIGS. 7A and 7B.

Synthesis of GO and deposition of GO onto QUANTIFOIL™ EM grids (Quantifoil Micro Tools Gmbh, Germany) were described as above. Surface modification of GO was designed via the nucleophilic ring opening of epoxy groups by primary amines. GO grids were submerged in 30 μl of ethylenediamine solution in dimethyl sulfoxide (DMSO) with a concentration of 10 mM and gently shaken for 5 hours. The grids were rinsed thoroughly by deionized (DI) water and ethanol sequentially and dried in ambient conditions. The configuration of GO-amino grids is depicted in FIG. 7A. For GO-PEG-amino grids (FIG. 7B), GO grids were submerged in amine-PEG-amine (molecular weight 5k) solution in DMSO with a concentration of 1 mM and gently shaken overnight. After washing with DI water and ethanol, the GO-PEG-amino grids were dried in ambient conditions. Both kinds of grids can be stored at −20° C. for months.

As described above, GO deposition using the Langmuir-Blodgett method produced robust and satisfying coating. It was estimated that GO covered over 90% of the grid surface, with at least 40% being monolayer, about 40% bilayer and rest having three layers. Coating of GO with more than three layers is very rare.

Test specimens included the complex between bacterial Hsp90 and bacterial ribosomal protein L2 (~170 kDa) to illustrate the performance of the GO-amino grid in improving protein distribution. On standard grids, no particles were observed inside the grid holes using complex concentrations as high as 10 μM. The same sample shows high particle density when applied to the GO-amino grids in concentrations as low as 250 nM, with excellent distribution, recognizable particles and producing good 2D classes, as confirmed by Cryo-EM micrographs.

Another example representative of particle distribution improvement was demonstrated using DNA origami as a specimen. To control the side DNA origami structures deposited on a cryo-EM grid, it is essential to have a support film on grid surface. Although a thin layer of amorphous carbon or GO film may both serve as the substrate, it was found that DNA origami structures deform and make large aggregates on QUANTIFOIL™ grids with thin amorphous carbon or GO film. On the other hand, mono dispersed DNA origami structures were observed on GO-amino grids, which remained folded and deposited majorly on their large area flat surfaces.

In another test of the GO-amino grids, the avb8/L-tgfB complex was tested, which showed a set of strongly preferred orientations (predominantly side views) when frozen on traditional holey carbon grids at a concentration of 0.25 mg/ml. This resulted in 3D maps that were overestimated in resolution and highly "stretched" likely due to overfitting artifacts. The complex frozen on GO-amino grids (0.075 mg/ml) provided a greater number of orientations and a wider distribution than the holey carbon grids, as reflected on the heat map.

The orientation change was also illustrated in testing the protein TRPA1 as a test specimen. This protein adopted only top views on regular holey carbon grids, preventing 3D structure determination. In order to acquire side views necessary for calculating the 3D structure, the TRPA1 sample was prepared on GO-amino grids. TRPA1 particles adhered to the grids with a side view orientation. A 3D map of TRPA1 was then determined to ~3.5 Å resolution by combining both orientations.

Figure 7B:
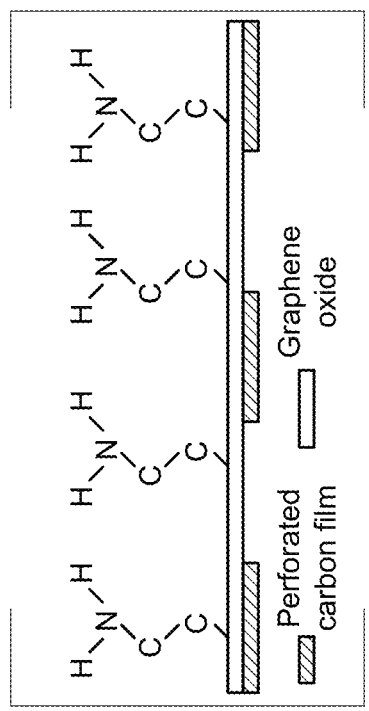

Considering that most particles dwell at the air-water interface with conventional holey carbon grids, it is reasonable to assume the orientation change was caused by the shift in particle location, which was confirmed by tomography analysis. On the GO-amino grid, indeed the vast majority of protein particles were pulled away from the air-water interface, with the bottom layer of particles around 5 nm from the GO surface. The particles stacked continuously spanning a distance of 20 nm. It is noticeable that a few particles were extremely close to the GO surface with distances of around 5 nm. It is also possible that some particles were already in contact with the GO surface. In order to keep particles away from both the air-water interface and the GO surface, a PEG spacer was introduced between the two ending amino groups (FIG. 7B). As a result, with the same amount of protein applied, few particles were found to stick to the GO surface while particle stacking remained around 20 nm from the GO surface, and far below the air-water interface.

In summary, the GO grids with amino functionalization provided enrichment in a general fashion. The grid surface wettability as well as the protein distribution were greatly improved. Moreover, particle orientation could be changed due to the capability of the GO-amino grid pulling particles away from the air-water interface. Addition of a PEG spacer kept particles away from both the air-water interface and the GO surface, which protects delicate samples from partial denaturation and aggregation.

Exemplary Embodiments

In one embodiment, the scope of the invention encompasses a graphene-coated cryo-EM sample grid comprising a substrate, the substrate comprising a perforated substrate comprising a plurality of holes and comprising, in various embodiments amorphous carbon, carbon coated material, gold, gold coated material, or silicon nitride, the graphene oxide coating comprising, for example, a single layer of graphene oxide or three or less layers of graphene oxide over a substantial portion of the substrate, for example, the single layer or 1-3 layers covering at least 25%, at least 40%, at least 50% or greater coverage of the substrate, wherein the graphene oxide film is functionalized with a plurality of affinity moieties. In one embodiment, the affinity moieties are joined to the graphene oxide film by amine reactions with epoxide groups present on the graphene oxide films.

In various embodiments, the graphene oxide is joined to the graphene oxide film by a construct comprising an intervening spacer, wherein the intervening spacer comprises a spacer composition, for example, a spacer composition that prevents substantial interaction between sample molecules associated with the grid by the affinity moieties and the substrate. In various embodiments, the spacer moiety comprises a polyethylene, a polyester, a polyether, polyalcohol, poly(N-isopropylacrylamide) (PNIPAM), polyacrylamide (PAM); poly(acrylic acid); polymethacrylate or another acrylic polymer; or polyethylene glycol (PEG). In various embodiments the average size of the intervening spacer is in the range of 100 to 50,000 Daltons, for example, 500-5,000 Daltons. In various embodiments, the spacer has an average molecular weights of about 100, 500, 600, 750, 1,000, 2,000, 3,0000, 4,000, 5,000, 6,000, 7,000, 8,000, 9,000, 10,000, or 20,000 Daltons.

In some embodiments, the intervening spacer is PEG, in various embodiments being PEG having an average size in the range of 100 to 50,000 Daltons, for example, 500-5,000 Daltons. In various embodiments, the spacer has an average molecular weights of about 100, 500, 600, 750, 1,000, 2,000, 3,0000, 4,000, 5,000, 6,000, 7,000, 8,000, 9,000, 10,000, or 20,000 Daltons.

In various embodiments, the affinity moiety is an amine, in various embodiments being a primary amine, secondary amine, or tertiary amine. In one embodiment, the affinity group comprises a peptide or protein. In various embodiments, the peptide or protein is a receptor, a ligand for a receptor, an antibody or antigen binding fragment thereof. In various embodiments, the affinity group comprises one binding partner from a tagging system, in various embodiments, the tagging system being the SpyCatcher-SpyTag, SnoopCatcher-SnoopTag tagging system, the HaloTag tagging system, a split GFP tagging system; the DogTag tagging system; the Isopeptag tagging system; the SdyTag tagging system; a biotin-avidin tagging system; a strepavidin-biotin tagging system; and a polyhistidine tagging system.

In one embodiment the affinity moiety is a SpyCatcher protein. In one embodiment the SpyCatcher protein is SEQ ID NO: 2 or a variant thereof. In one embodiment the affinity moiety is a SpyTag peptide. In one embodiment, the SpyTag peptide is SEQ ID NO: 1 or a variant thereof. In one embodiment, the affinity moiety comprises a SnoopCatcher protein. In one embodiment, the SnoopCatcher protein comprises SEQ ID NO: 3. In one embodiment, the affinity moiety comprises a SnoopTag peptide. In one embodiment, the SnoopTag peptide is SEQ ID NO: 4 or a variant thereof. In one embodiment, the affinity moiety comprises a HaloTag protein. In one embodiment, the HaloTag protein is SEQ ID NO: 5 or a variant thereof. In one embodiment, the affinity moiety is a chloroalkane ligand that, under suitable conditions, forms a covalent bond with a HaloTag protein.

In an exemplary embodiment, the scope of the invention encompasses a graphene-coated cryo-EM sample grid comprising a substrate, the substrate comprising a perforated substrate comprising a plurality of holes and comprising, in various embodiments amorphous carbon, carbon coated material, gold, gold coated material, or silicon nitride, optionally, the graphene oxide coating comprising, a single layer of graphene oxide or three or less layers of graphene oxide over a substantial portion of the substrate, for example, the single layer or 1-3 layers covering at least 25%, at least 40%, at least 50% or greater coverage of the substrate, wherein the graphene oxide film is functionalized with a plurality of affinity moieties comprising amines, in various embodiments being primary amines, secondary amines, or tertiary amines; optionally, wherein the binding partner is joined to the graphene oxide by a spacer composition, in various embodiments the spacer composition having an average molecular weight of 100 to 50,000 Daltons, in various embodiments being 500 to 5,000 Daltons, in various embodiments, the spacer composition comprising polyethylene, a polyester, a polyether, polyalcohol, PNIPAM, PAM; poly(acrylic acid); polymethacrylate or another acrylic polymer; or PEG. In one embodiment, the spacer composition is PEG.

In an exemplary embodiment, the scope of the invention encompasses a graphene-coated cryo-EM sample grid comprising a substrate, the substrate comprising a perforated substrate comprising a plurality of holes and comprising, in various embodiments amorphous carbon, carbon coated material, gold, gold coated material, or silicon nitride, optionally, the graphene oxide coating comprising a single layer of graphene oxide or three or less layers of graphene oxide over a substantial portion of the substrate, for example, the single layer or 1-3 layers covering at least 25%, at least 40%, at least 50% or greater coverage of the substrate, optionally, wherein the binding partner is joined to the graphene oxide by a spacer composition, in various embodiments the spacer composition having an average molecular weight of 100 to 50,000 Daltons, in various embodiments being 500 to 5,000 Daltons, in various embodiments, the spacer composition comprising polyethylene, a polyester, a polyether, polyalcohol, PNIPAM, PAM; poly(acrylic acid); polymethacrylate or another acrylic polymer; or PEG. In one embodiment, the spacer composition is PEG.

In an exemplary embodiment, the scope of the invention encompasses a graphene-coated cryo-EM sample grid comprising a substrate, the substrate comprising a perforated substrate comprising a plurality of holes and comprising, in various embodiments amorphous carbon, carbon coated material, gold, gold coated material, or silicon nitride, optionally, the graphene oxide coating comprising, for example, a single layer of graphene oxide or three or less layers of graphene oxide over a substantial portion of the substrate, for example, the single layer or 1-3 layers covering at least 25%, at least 40%, at least 50% or greater coverage of the substrate; wherein the graphene oxide film is functionalized with a plurality of affinity moieties comprising an antibody or antibody fragment, a receptor or receptor ligand, or one binding partner of a tagging system;

optionally, wherein the binding partner is joined to the graphene oxide by a spacer composition, in various embodiments the spacer composition having an average molecular weight of 100 to 50,000 Daltons, in various embodiments being 500 to 5,000 Daltons, in various embodiments, the spacer composition comprising polyethylene, a polyester, a polyether, polyalcohol, PNIPAM, PAM; poly(acrylic acid); polymethacrylate or another acrylic polymer; or PEG. In one embodiment, the spacer composition is PEG.

In an exemplary embodiment, the scope of the invention encompasses a graphene-coated cryo-EM sample grid comprising a substrate, the substrate comprising a perforated substrate comprising a plurality of holes and comprising, in various embodiments amorphous carbon, carbon coated material, gold, gold coated material, or silicon nitride; optionally, the graphene oxide coating comprising, for example, a single layer of graphene oxide or three or less layers of graphene oxide over a substantial portion of the substrate, for example, the single layer or 1-3 layers covering at least 25%, at least 40%, at least 50% or greater coverage of the substrate; wherein the graphene oxide film is functionalized with a plurality of affinity moieties comprising any of a SpyCatcher protein, a SpyTag peptide, a SnoopCatcher protein, a SnoopTag peptide, a HaloTag protein, or a chloroalkane ligand of HaloTag protein, a protein or peptide of SEQ ID NO: 1, or a variant thereof; a protein or peptide of SEQ ID NO: 2, or a variant thereof; a protein or peptide of SEQ ID NO: 3, or a variant thereof; a protein or peptide of SEQ ID NO: 4, or a variant thereof; a protein or peptide of SEQ ID NO: 5, or a variant thereof; optionally, wherein the binding partner is joined to the graphene oxide by a spacer composition, in various embodiments the spacer composition having an average molecular weight of 100 to 50,000 Daltons, in various embodiments being 500 to 5,000 Daltons, in various embodiments, the spacer composition comprising polyethylene, a polyester, a polyether, polyalcohol, PNIPAM, PAM; poly(acrylic acid); polymethacrylate or another acrylic polymer; or PEG. In one embodiment, the spacer composition is PEG.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A functionalized cryo-EM substrate, wherein
the substrate comprises a plurality of holes or openings;
at least 50% of the holes are covered by a graphene oxide film comprising 1-3 layers of graphene sheets; and
the graphene oxide film is functionalized with:
an affinity moiety that promotes the association of a target specimen to the substrate; or
a functional moiety that facilitates the conjugation of affinity moieties to the substrate.

2. The cryo-EM substrate of claim 1, wherein the cryo-EM substrate comprises amorphous carbon, amorphous carbon coated material, gold, gold-coated material, or silicon nitride.

3. The cryo-EM substrate of claim 1, wherein at least seventy percent of the hole area of the substrate is covered by the graphene oxide film.

4. The cryo-EM substrate of claim 1, wherein at least 80% of the substrate is covered by the graphene oxide film.

5. The cryo-EM substrate of claim 1, wherein the target specimen is selected from the group consisting of a protein, an organelle, a virus, and a cell.

6. The cryo-EM substrate of claim 1, further comprising an intervening spacer, and wherein the affinity moiety or functional moiety is conjugated to the graphene oxide film by the intervening spacer.

7. The cryo-EM substrate of claim 6, wherein the intervening spacer comprises a composition selected from the group consisting of an alkyl chain, a polyester, a polyether, a polyalcohol, and a polyglycol, PNIPAM, PAM; poly (acrylic acid); polymethacrylate, an acrylic polymer; and PEG.

8. The cryo-EM substrate of claim 1, wherein the affinity moiety comprises one binding partner of a tagging system, wherein the tagging system comprises two compositions comprising a first and a second binding partner, and wherein, under suitable conditions, the first and the second binding partner will form a covalent bond.

9. The cryo-EM substrate of claim 8, wherein the binding partner of a tagging system is selected from the group consisting of: a SpyCatcher protein; a SpyTag protein; a SnoopCatcher protein; a SnoopTag protein; a HaloTag protein; a chloroalkane ligand configured to covalently bond with a HaloTag; a split; a binding partner of the DogTag tagging system; a binding partner of the Isopeptag tagging system; a binding partner of the SdyTag tagging system; biotin; avidin; streptavidin; and a polyhistidine tag.

10. The cryo-EM substrate of claim 1, wherein the affinity moiety is selected from the group consisting of an amine, a peptide, an antibody or antigen binding fragment thereof, and a nucleic acid.

11. The cryo-EM substrate of claim 1, wherein the substrate is functionalized with a functional moiety that facilitates the conjugation of affinity moieties to the substrate; and wherein the functional moiety comprises a composition selected from the group consisting of an amine; an alkyne; maleimide; NHS, or sulfo-NHS.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      SpyTag peptide

<400> SEQUENCE: 1

Val Pro Thr Ile Val Met Val Asp Ala Tyr Lys Arg Tyr Lys Cys
1               5                   10                  15

<210> SEQ ID NO 2
<211> LENGTH: 139
<212> TYPE: PRT
<213> ORGANISM: Artificial Sequence
<220> FEATURE:
<223> OTHER INFORMATION: Description of Artificial Sequence: Synthetic
      Spycatcher protein sequence

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Val Asp Thr Leu Ser Gly
                20                  25                  30

Leu Ser Ser Glu Gln Gly Gln Ser Gly Asp Met Thr Ile Glu Glu Asp
            35                  40                  45

Ser Ala Thr His Ile Lys Phe Ser Lys Arg Asp Glu Asp Gly Lys Glu
        50                  55                  60

Leu Ala Gly Ala Thr Met Glu Leu Arg Asp Ser Ser Gly Lys Thr Ile
65                  70                  75                  80

Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110
```

```
Ala Thr Ala Ile Thr Phe Thr Val Asn Glu Gln Gly Gln Val Thr Val
        115                 120                 125

Asn Gly Lys Ala Thr Lys Gly Asp Ala His Ile
    130                 135

<210> SEQ ID NO 3
<211> LENGTH: 133
<212> TYPE: PRT
<213> ORGANISM: Artificial Sequence
<220> FEATURE:
<223> OTHER INFORMATION: Description of Artificial Sequence: Synthetic
      Snoopcatcher protein

<400> SEQUENCE: 3

Met Gly Ser Ser His His His His His His Ser Ser Gly Leu Val Pro
1               5                   10                  15

Arg Gly Ser His Met Lys Pro Leu Arg Gly Ala Val Phe Ser Leu Gln
            20                  25                  30

Lys Gln His Pro Asp Tyr Pro Asp Ile Tyr Gly Ala Ile Asp Gln Asn
        35                  40                  45

Gly Thr Tyr Gln Asn Val Arg Thr Gly Glu Asp Gly Lys Leu Thr Phe
    50                  55                  60

Lys Asn Leu Ser Asp Gly Lys Tyr Arg Leu Phe Glu Asn Ser Glu Pro
65                  70                  75                  80

Ala Gly Tyr Lys Pro Val Gln Asn Lys Pro Ile Val Ala Phe Gln Ile
                85                  90                  95

Val Asn Gly Glu Val Arg Asp Val Thr Ser Ile Val Pro Gln Asp Ile
            100                 105                 110

Pro Ala Thr Tyr Glu Phe Thr Asn Gly Lys His Tyr Ile Thr Asn Glu
        115                 120                 125

Pro Ile Pro Pro Lys
    130

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      Snooptag sequence

<400> SEQUENCE: 4

Lys Leu Gly Asp Ile Glu Phe Ile Lys Val Asn Lys
1               5                   10

<210> SEQ ID NO 5
<211> LENGTH: 296
<212> TYPE: PRT
<213> ORGANISM: Artificial Sequence
<220> FEATURE:
<223> OTHER INFORMATION: Description of Artificial Sequence: Synthetic
      Halo tag protein

<400> SEQUENCE: 5

Met Gly Ser Glu Ile Gly Thr Gly Phe Pro Phe Asp Pro His Tyr Val
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45
```

-continued

```
Trp Arg Asn Ile Ile Pro His Val Ala Pro Ser His Arg Cys Ile Ala
    50              55                  60

Pro Asp Leu Ile Gly Met Gly Lys Ser Asp Lys Pro Asp Leu Asp Tyr
65              70                  75                  80

Phe Phe Asp Asp His Val Arg Tyr Leu Asp Ala Phe Ile Glu Ala Leu
            85                  90                  95

Gly Leu Glu Glu Val Val Leu Val Ile His Asp Trp Gly Ser Ala Leu
            100                 105                 110

Gly Phe His Trp Ala Lys Arg Asn Pro Glu Arg Val Lys Gly Ile Ala
        115                 120                 125

Cys Met Glu Phe Ile Arg Pro Ile Pro Thr Trp Asp Glu Trp Pro Glu
    130                 135                 140

Phe Ala Arg Glu Thr Phe Gln Ala Phe Arg Thr Ala Asp Val Gly Arg
145             150                 155                 160

Glu Leu Ile Ile Asp Gln Asn Ala Phe Ile Glu Gly Ala Leu Pro Met
            165                 170                 175

Gly Val Val Arg Pro Leu Thr Glu Val Glu Met Asp His Tyr Arg Glu
            180                 185                 190

Pro Phe Leu Lys Pro Val Asp Arg Glu Pro Leu Trp Arg Phe Pro Asn
        195                 200                 205

Glu Leu Pro Ile Ala Gly Glu Pro Ala Asn Ile Val Ala Leu Val Glu
    210                 215                 220

Ala Tyr Met Asn Trp Leu His Gln Ser Pro Val Pro Lys Leu Leu Phe
225             230                 235                 240

Trp Gly Thr Pro Gly Val Leu Ile Pro Pro Ala Glu Ala Ala Arg Leu
            245                 250                 255

Ala Glu Ser Leu Pro Asn Cys Lys Thr Val Asp Ile Gly Pro Gly Leu
            260                 265                 270

Phe Leu Leu Gln Glu Asp Asn Pro Asp Leu Ile Gly Ser Glu Ile Ala
        275                 280                 285

Arg Trp Leu Pro Gly Leu Ala Gly
290             295
```